(12) United States Patent
Rock et al.

(10) Patent No.: US 7,777,156 B2
(45) Date of Patent: Aug. 17, 2010

(54) ELECTRIC HEATING/WARMING FABRIC ARTICLES

(75) Inventors: Moshe Rock, Brookline, MA (US); Vincent Doyle, III, Pelham, NH (US)

(73) Assignee: MMI-IPCO, LLC, Lawrence, MA (US)

( * ) Notice: Subject to any disclaimer, the term of this patent is extended or adjusted under 35 U.S.C. 154(b) by 717 days.

(21) Appl. No.: 11/683,171

(22) Filed: Mar. 7, 2007

(65) Prior Publication Data

US 2007/0164010 A1   Jul. 19, 2007

Related U.S. Application Data

(63) Continuation-in-part of application No. 11/145,830, filed on Jun. 6, 2005, now Pat. No. 7,268,320, which is a continuation-in-part of application No. 10/927,665, filed on Aug. 27, 2004, now Pat. No. 7,202,443, which is a continuation-in-part of application No. 10/339,083, filed on Jan. 9, 2003, now abandoned.

(60) Provisional application No. 60/386,180, filed on Jan. 14, 2002.

(51) Int. Cl.
    *H05B 3/00* (2006.01)
(52) U.S. Cl. .................. 219/212; 219/211; 219/528; 219/544; 219/549
(58) Field of Classification Search .............. 219/545, 219/544, 211, 212, 528
    See application file for complete search history.

(56) References Cited

U.S. PATENT DOCUMENTS

| | | |
|---|---|---|
| 2,277,772 A | 3/1942 | Marick |
| 2,713,193 A | 7/1955 | Robbins et al. |
| 3,513,297 A | 5/1970 | Jordan |
| 3,539,767 A | 11/1970 | Eisler |
| 3,564,206 A | 2/1971 | Lauck |
| 3,697,728 A | 10/1972 | Stirzenbecher |
| 3,729,613 A | 4/1973 | Deloire et al. |
| 3,745,301 A | 7/1973 | Sherrill et al. |
| 3,751,620 A | 8/1973 | Yuasa .................. 219/211 |
| 3,869,596 A | 3/1975 | Howie |

(Continued)

FOREIGN PATENT DOCUMENTS

DE          33 34 744          4/1984

(Continued)

*Primary Examiner*—Tu B Hoang
*Assistant Examiner*—Vinod D Patel
(74) *Attorney, Agent, or Firm*—Fish & Richardson P.C.

(57) ABSTRACT

Electric heating/warming composite fabric articles have at least a fabric layer having inner and outer surfaces, and an electric heating/warming element, e.g., including a bus, formed, e.g., of die cut metallized textile or plastic sheeting or metal foil, affixed at a surface of the fabric layer and adapted to generate heating/warming when connected to a power source. A air-and-water droplet resistant and water vapor permeable barrier layer may be positioned, for example, adjacent to the fabric layer; e.g., with the electric heating/warming element formed thereupon or at least partially impregnated therein, e.g. in a fabric laminate or in a composite formed by application of heat and pressure to at least one layer of a barrier film disposed adjacent thereto, including to protect the electric circuit, e.g. against abrasion, moisture, and or against physical stress due, e.g., to repeated crushing, bending or flexing. Methods of forming electric heating/warming composite fabric articles are described and claimed.

35 Claims, 17 Drawing Sheets

U.S. PATENT DOCUMENTS

| | | |
|---|---|---|
| 3,978,183 A | 8/1976 | Erickson |
| 3,999,037 A | 12/1976 | Metcalf, Sr. |
| 4,021,640 A | 5/1977 | Gross et al. |
| 4,044,221 A | 8/1977 | Kuhn |
| 4,061,898 A | 12/1977 | Murray et al. |
| 4,065,660 A | 12/1977 | Berard |
| 4,147,921 A | 4/1979 | Walter et al. |
| 4,245,149 A | 1/1981 | Fairlie |
| 4,272,673 A | 6/1981 | Semanaz et al. |
| 4,320,286 A | 3/1982 | Borrup |
| 4,485,297 A | 11/1984 | Grise et al. |
| 4,590,359 A | 5/1986 | Mobius |
| 4,656,339 A | 4/1987 | Grise |
| 4,700,054 A | 10/1987 | Triplett et al. ............... 219/545 |
| 4,713,531 A | 12/1987 | Fennekels et al. |
| 4,736,088 A | 4/1988 | Bart |
| 4,764,665 A | 8/1988 | Orban et al. |
| 4,774,397 A | 9/1988 | Grise |
| 4,814,586 A | 3/1989 | Grise |
| 4,849,255 A | 7/1989 | Grise et al. |
| 4,857,384 A | 8/1989 | Mio et al. |
| 4,888,089 A | 12/1989 | Marstiller et al. |
| 4,892,998 A | 1/1990 | Marstiller et al. |
| 4,912,306 A | 3/1990 | Grise et al. |
| 4,948,951 A | 8/1990 | Balzano |
| 4,950,868 A | 8/1990 | Moss et al. |
| 4,983,814 A | 1/1991 | Ohgushi et al. |
| 5,019,797 A | 5/1991 | Marstiller et al. |
| 5,032,705 A | 7/1991 | Batcheller et al. |
| 5,081,339 A | 1/1992 | Stine |
| 5,148,002 A | 9/1992 | Kuo et al. |
| 5,151,578 A | 9/1992 | Phillips |
| 5,298,722 A | 3/1994 | Tanaka |
| 5,302,807 A | 4/1994 | Zhao |
| 5,364,678 A | 11/1994 | Lumb et al. |
| 5,413,837 A | 5/1995 | Rock et al. .................. 428/192 |
| 5,422,462 A | 6/1995 | Kishimoto .................. 219/545 |
| 5,432,322 A | 7/1995 | Ingram et al. |
| 5,484,983 A | 1/1996 | Roell |
| 5,541,388 A | 7/1996 | Gadd |
| 5,547,733 A | 8/1996 | Rock et al. |
| 5,679,377 A | 10/1997 | Niibe et al. |
| 5,804,798 A | 9/1998 | Takeda |
| 5,824,996 A | 10/1998 | Kochman et al. |
| 5,925,275 A | 7/1999 | Lawson et al. |
| 6,060,693 A | 5/2000 | Brown |
| 6,097,009 A | 8/2000 | Cole |
| 6,111,233 A | 8/2000 | Rock et al. |
| 6,218,644 B1 | 4/2001 | Zorn et al. |
| 6,229,123 B1 | 5/2001 | Kochman et al. |
| 6,239,410 B1 | 5/2001 | Tackore |
| 6,268,595 B1 | 7/2001 | Haenel |
| 6,331,695 B1 | 12/2001 | West |
| 6,389,681 B1 | 5/2002 | Rock et al. |
| 6,483,087 B2 | 11/2002 | Gardner et al. |
| 2001/0019050 A1 | 9/2001 | Rock et al. .................. 219/545 |
| 2004/0045955 A1 | 3/2004 | Rock et al. |

FOREIGN PATENT DOCUMENTS

| | | |
|---|---|---|
| DE | 197 45 889 | 4/1999 |
| EP | 0 571 978 | 1/1993 |
| EP | 1 021 064 | 7/2000 |
| GB | 581 212 | 10/1946 |
| GB | 587 189 | 4/1947 |
| GB | 653 641 | 5/1951 |

ELECTRIC HEATING/WARMING FABRIC ARTICLES

CROSS-REFERENCE TO RELATED APPLICATIONS

This application is a continuation-in-part application of U.S. patent application Ser. No. 11/145,830, filed Jun. 6, 2005, now U.S. Pat. No. 7,268,320, which is a continuation-in-part application of U.S. patent application Ser. No. 10/927,665, now U.S. Pat. No. 7,202,443 filed Aug. 27, 2004, which is a continuation-in-part application of U.S. patent application Ser. No. 10/339,083, filed Jan. 9, 2003, now pending, which claims benefit from U.S. Application No. 60/386,180, filed Jan. 14, 2002, now abandoned. Each of these applications is expressly incorporated by reference herein in its entirety.

TECHNICAL FIELD

The disclosure relates to electrical resistance heating/warming textile articles.

BACKGROUND

Techniques known for augmenting heating/warming capabilities of clothing fabric include adding electric wires to the fabric, typically by incorporating the wires directly into the fabric or by attaching the wires to the fabric, e.g., by sewing. It is also known, e.g., from Gross et al. U.S. Pat. No. 4,021,640, to print an electrical circuit with a resistance heating element on a plastic sheet, such as MYLAR®, and to incorporate strips of the plastic sheet into a fabric article, such as a glove.

SUMMARY

In one aspect, a method of forming an electric heating/warming fabric article comprises configuring a planar, sheet-form conductive layer element including a bus, formed of electrically conductive material selected from the group consisting of metallized textile, metallized plastic sheeting, and metal foil, into an electrically conductive circuit with shape corresponding to a selected surface region of a wearer's body, with one or more circuit regions of relatively higher resistivity among one or more circuit regions of relatively lower resistivity, the one or more circuit regions of relatively higher resistivity positioned for correlation with one or more selected heating regions of the wearer's body; attaching the circuit to at least one of a first broad surface and a second broad surface of a fabric body in an arrangement corresponding to the selected surface region and in correlation with the one or more selected heating regions; and, upon application of electrical current to the circuit, producing localized heating in the one or more circuit regions of relatively higher resistivity of the circuit attached upon the fabric body for preferential heating of the one or more selected heating regions of the wearer's body.

Using a sheet-form conductive layer to form the circuit provides a robust, flat, and pliable heating/warming element that can be easily manufactured and readily attached to a textile to form a fabric article. The flexible nature of the conductive layer provides good dexterity when the heating/warming element is used in a glove or other article of clothing in which flexibility is useful. The sheet-form conductive layer can also be readily configured in various circuits and geometries, e.g., to provide differential heating to different areas of an article, as will be discussed further below.

Some implementations of this aspect may include one or more of the following features. The planar, sheet-form conductive layer element is impregnated with an integral bus. The electrically conductive metallized textile is impregnated with a suitable thermoplastic polymeric material to lock fibers of the electrically conductive metallized textile in a manner to resist local increase in resistivity due to physical stress from one or more of repeated crushing, bending and flexing. The suitable thermoplastic polymeric material is applied in fluid state or hot melt and forming a fabric laminate incorporating the impregnated electrically conducting metallized textile. The laminate is a woven fabric, preferably a lightweight woven fabric stable in warp and fill directions. The metallized textile may be at least partially impregnated by application of predetermined conditions of heat, pressure and time to at least one layer of the suitable thermoplastic polymeric material in the form of a film disposed adjacent the metallized textile to be at least partially impregnated, e.g. by applying heat of about 350° F. at pressure of about 7 psi for about 50 seconds. The metallized textile may be at least partially impregnated with a suitable thermoplastic polymeric barrier material that has characteristics of being air-and-water-droplet resistant and being water vapor permeable, e.g. urethane. Configuring comprises die-cutting or subjecting a sheet material to metal coating, plating or deposition. Attaching comprises joining the conductive layer and fabric body with adhesive. The term "adhesive," as used herein, refers to any material that will join the layers, including both liquid adhesives and non-liquid, flowable materials such as hot melt webs (commercially available, e.g., from Bostik Co.).

The method further comprises forming an article of clothing including the fabric body. Forming comprises shaping the circuit to conform to the shape of the article of clothing selected, e.g., from the group consisting of gloves, socks, sweaters, jackets, shirts, pants, hats, footwear, ear muffs, neck warmers, medical braces, medical bands, knee pads, back pads, and joint pads. Forming comprises shaping the circuit to conform, e.g., to the shape of a glove, to the shape of an article of footwear, or to the shape of a garment, such as a shirt or jacket.

In some implementations, by varying the effective electricity-conducting volume, e.g., the cross-sectional area, of the heating/warming element in selected regions, the level of heat generation can be locally controlled. (For heating/warming elements of uniform thickness, e.g., those formed of metal foil, the effective volume is typically adjusted by variation of the width and/or length.) For example, in a heating/warming element for use in a shoe, the volume of the heating/warming element in the region of the toes may preferably be less than its volume in the heel region, thus creating greater resistivity in the region of the toes and greater heat generation. Similarly, for use in gloves, the effective volume of the heating/warming element in the region of the fingers will preferably be less (for greater resistivity and heat generation) than in the palm region.

The method comprises providing circuit regions of relatively higher resistivity comprises by reducing the cross-sectional area of one or more selected regions of the circuit. The method comprises providing circuit regions of relatively higher resistivity comprises by reducing the conductivity of one or more selected regions of the circuit. The electric heating/warming article is incorporated into an article of clothing, and the method further comprises positioning the one or more circuit regions of relatively higher resistivity for correlation with one or more selected heating regions of the wearer's body adjacent the wearer's extremities when the article of clothing is worn. The method further comprises incorporating the electric heating/warming article into an article of clothing, and positioning the one or more circuit regions of relatively higher resistivity for correlation with one or more selected heating regions of the wearer's body adjacent regions of the wearer's body where blood flow is close to the skin surface when the article of clothing is worn. This allows more heat to be delivered to the extremities, which are prone to vasorestriction in cold weather.

In some instances, heat can be provided to a user's extremities by providing heat to a region through which a large volume of blood supply flows, for example the wrist. In general, an area of relatively high resistivity can be provided adjacent to a major blood vessel or vessels larger than capillaries that pass sufficiently near the skin surface. Accordingly, heat may be conducted directly from the surface of the skin into the blood flowing through the major blood vessel or vessels toward a body extremity, providing heat to the extremity.

The method also includes attaching the circuit to at least one broad surface of a fabric body comprising a textile material selected from the group consisting of weft knitted materials, warp knitted materials, woven materials, and nonwoven materials. The method may also include interposing a barrier layer between the fabric body and the sheet-form conductive layer, e.g., by interposing an air-and-water-droplet resistant, water vapor permeable barrier layer between the fabric body and the sheet-form conductive layer. The method further comprises attaching an outer surface of the air-and-water-droplet resistant, water vapor permeable barrier layer to the fabric layer, and attaching an inner surface of the barrier layer to the sheet-form conductive layer. Attaching comprises joining the layers with adhesive. A barrier is generally used in situations where wind protection is desired.

The method further includes connecting the circuit to a power source, to generate heating/warming. The method further comprises incorporating the electric heating/warming fabric article into a home furnishing textile article, e.g. a blanket, throw, sleeping bag or mattress cover. Configuring of the circuit comprises configuring the circuit as a series circuit, or as a parallel circuit. The method further comprises providing to at least one of the first broad surface and the second broad surface of the fabric body with a smooth surface, a raised surface, or a brushed surface.

In another aspect, a method of forming an electric heating/warming fabric article, the method comprises: configuring a planar, sheet-form conductive layer element, formed of electrically conductive material selected from the group consisting of metallized textile, metallized plastic sheeting, and metal foil, into an electrically conductive circuit with shape corresponding to a selected surface region of a wearer's body and with one or more circuit regions of relatively higher resistivity among one or more circuit regions of relatively lower resistivity, the one or more circuit regions of relatively higher resistivity positioned for correlation with one or more selected heating regions of the wearer's body; attaching the circuit to at least one of a first broad surface and a second broad surface of a fabric body in an arrangement corresponding to the selected surface region and in correlation with the one or more selected heating regions; attached a bus in communication with the circuit; and, upon application of electrical current through the bus to the circuit, producing localized heating in the one or more circuit regions of relatively higher resistivity of the circuit attached upon the fabric body for preferential heating of the one or more selected heating regions of the wearer's body.

In another aspect, a method of forming an electric heating/warming fabric article comprises, e.g., die-cutting, laser cutting, manual cutting or stamping a sheet-form conductive layer to form an electrically conductive circuit including a bus wherein a first portion of the conductive layer is relatively narrower to increase localized heating and a second portion of the conductive layer is relatively wider to decrease localized heating; attaching the circuit to an outer surface of a fabric body; incorporating the fabric body into an article of clothing; and connecting a power source to the circuit, thereby producing localized heating of the fabric body upon application of electrical current to the circuit.

In another aspect, a method of forming an electric heating/warming fabric article, the method comprises: die-cutting a sheet-form conductive layer to form an electrically conductive circuit, wherein a first portion of the conductive layer is relatively narrower to increase localized heating and a second portion of the conductive layer is relatively wider to decrease localized heating; attaching the circuit to an outer surface of a fabric body; attaching a bus in communication with the circuit; incorporating the fabric body into an article of clothing; and connecting a power source to the bus and the circuit, thereby producing localized heating of the fabric body upon application of electrical current to the circuit.

In yet another aspect, a heating/warming fabric article comprises a fabric layer having a broad first surface and a broad second surface, and, attached to at least one of the broad first surface and the broad second surface, a planar, sheet-form conductive layer element, formed of material selected from the group consisting of metallized textile, metallized plastic sheeting, and metal foil, formed into an electrically conductive circuit with shape corresponding to a selected surface region of a wearer's body and with one or more circuit regions of relatively higher resistivity among one or more circuit regions of relatively lower resistivity, the one or more circuit regions of relatively higher resistivity positioned for correlation with one or more selected heating regions of the wearer's body, the sheet-form conductive layer element, upon application of electrical current to the circuit, producing localized heating in the one or more circuit regions of relatively higher resistivity of the circuit attached upon the fabric body for preferential heating of the one or more selected heating regions of the wearer's body.

Some implementations of this aspect include one or more of the following features. The electrically conductive metallized textile is impregnated with a suitable thermoplastic polymeric material that locks fibers of the electrically conductive metallized textile in a manner to resist local increase in resistivity due to physical stress of one or more of repeated crushing, bending and flexing. The impregnated, electrically conductive metallized textile is incorporated in a fabric laminate. Preferably, the fabric laminate is a woven fabric laminate. More preferably, the woven fabric laminate is a lightweight woven fabric laminate stable in warp and fill directions. The metallized textile is at least partially impregnated with a suitable thermoplastic polymeric barrier material having characteristics of being air-and-water-droplet resistant and being water permeable, e.g. urethane. The fabric layer comprises a textile material selected from the group consisting of weft knitted materials, warp knitted materials, woven materials, and nonwoven materials. The fabric article comprises an article of clothing, e.g. selected from the group consisting of gloves, socks, sweaters, jackets, shirts, pants, hats, footwear, ear muffs, neck warmers, medical braces, medical bands, knee pads, back pads, and joint pads. The fabric article comprises a blanket, throw, sleeping bag or mattress cover. The heating/warming fabric article further comprises adhesive interposed between the conductive layer and fabric body. The article of clothing comprises an article.

The circuit includes areas of relatively higher resistivity and areas of relatively lower resistivity to provide regions of relatively higher localized heating and regions of relatively lower localized heating. The areas of relatively higher and relatively lower resistivity comprise regions of relatively lesser and relatively greater cross-sectional area, respectively. The fabric article comprises an article of clothing, and the one or more circuit regions of relatively higher resistivity positioned for correlation with one or more selected heating regions of the wearer's body is positioned adjacent a wearer's extremities when the article of clothing is worn. The fabric article comprises an article of clothing, and the one or more circuit regions of relatively higher resistivity positioned for correlation with one or more selected heating regions of the wearer's body is positioned adjacent regions of the wearer's body where arteries are close to the skin surface when the article of clothing is worn.

The heating/warming fabric article further comprises a barrier layer between the fabric layer and sheet-formed conductive layer. The barrier layer, fabric layer, and sheet-formed conductive layer are joined by adhesive. The circuit comprises a series circuit or a parallel circuit. The circuit is asymmetrical.

The heating/warming fabric article further comprises a temperature sensor for measuring the temperature of a portion of the circuit. The temperature sensor is configured to measure the temperature of a first portion of the circuit, and the first portion of the circuit is configured to have the same resistance as a second portion of the circuit, to allow the temperature of the second portion to be estimated by measuring the temperature of the first portion. For example, a first section can be positioned at the back of a glove with resistance similar to the resistance of a second section positioned in the extremities of the glove, for example the finger tips. The heating/warming fabric article further comprises a controller configured to adjust the power supplied to the circuit in response to changes in the measured temperature. For example, the temperature controller can be set to be activated if the temperature of the sensor drops below a setting. At least one of the inner surface and the outer surface of the fabric layer has a smooth surface or a raised surface or a brushed surface. The article of clothing includes one or more of the following: gloves, footwear, and/or a garment such as a shirt or jacket.

The details of one or more implementations are set forth in the accompanying drawings and the description below. Other features, objects, and advantages will be apparent from the description and drawings.

DESCRIPTION OF DRAWINGS

FIG. 12 is a somewhat diagrammatic exploded side edge view of components forming another implementation of a heating/warming composite fabric article constructed in accordance with the disclosure, while

FIGS. 24 and 24A are somewhat diagrammatic front plan and side section views of another implementation of an article of footwear with an electric heating/warming element of the disclosure.

FIGS. 25 and 25A are somewhat diagrammatic front plan and side section views of still another implementation of an article of footwear with an electric heating/warming element of the disclosure.

Like reference symbols in the various drawings indicate like elements.

DETAILED DESCRIPTION

This application relates to the disclosures of our prior co-pending patent applications U.S. application Ser. No. 09/298,722, filed Apr. 23, 1999; U.S. application Ser. No. 09/389,761, filed Sep. 9, 1999; U.S. Provisional Application No. 60/175,202, filed Jan. 10, 2000; U.S. Provisional Application No. 60/261,544, filed Jan. 12, 2001; U.S. Provisional Application No. 60/386,180, filed Jan. 14, 2002; U.S. patent application Ser. No. 10/339,083, filed Jan. 9, 2003; U.S. patent application Ser. No. 10/927,665, filed Aug. 27, 2004; and U.S. patent application Ser. No. 11/145,830, filed Jun. 6, 2005, the complete disclosure of each of which is incorporated herein by reference.

According to one preferred implementation, the heating/warming element 16 consists of die cut conductive sheet material, through which an electric current is conducted for producing local heating. The conductive sheet material may be, for example, a metallized sheet, e.g., a metallized textile or metallized plastic sheeting or a metal foil, or a conductive textile, e.g., a knitted, woven or non-woven material containing conductive fibers or yarns. The heating/warming element may be incorporated, e.g., directly or in the form of a textile laminate, into or upon articles of clothing or footwear, and into or upon home furnishings such as blankets and the like. Electric current, e.g. alternating current, via a power cord and plug, or direct current, via a battery, is then applied through the element to cause generation of heat, due to electric resistance.

Figure 1:
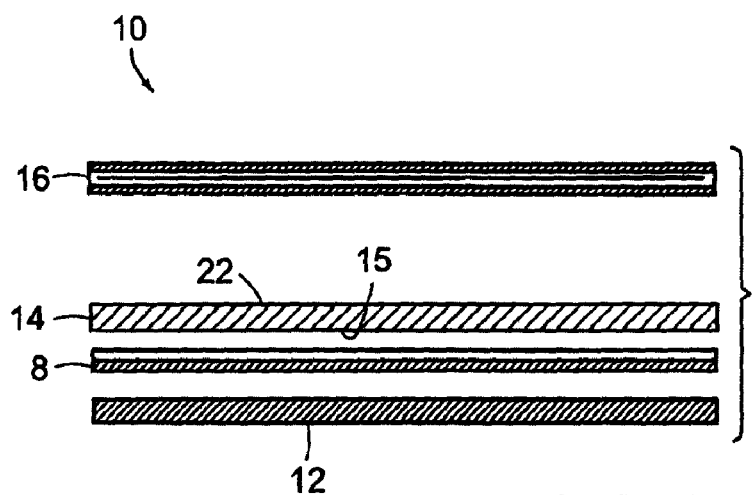
FIGS. 1 and 1A are somewhat diagrammatic exploded side edge views of the components forming the first implementations of a heating/warming composite fabric article constructed in accordance with the disclosure.
Figure 2:
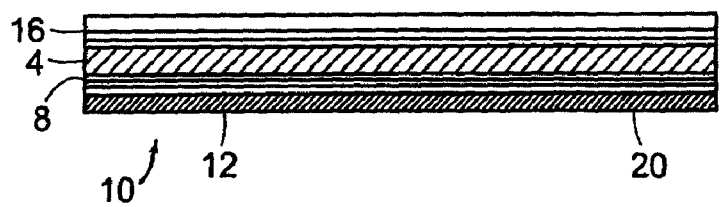
FIG. 2 is a somewhat diagrammatic side edge view of the heating/warming composite fabric article of FIG. 1.

Referring first to FIGS. 1 and 2, in a first implementation, a windproof, water-resistant, and vapor permeable electric heating/warming composite fabric article 10 constructed in accordance with this disclosure has three major components. These components include a fabric layer 12, a barrier layer 14 and an electric heating/warming element 16, wherein the fabric layer 12 and barrier layer 14 are joined at opposed fabric inner surface 13 and barrier outer surface 15, respectively, by adhesive 18.

Figure 1A:
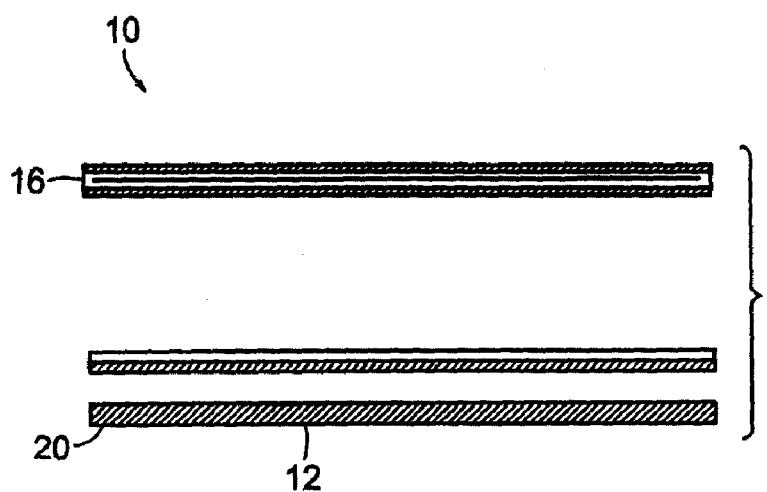

Referring to FIG. 1A, in another implementation the barrier layer 14 may be omitted. In this case, the electric heating/warming composite fabric article includes a fabric layer 12 and an electric heating/warming element 16. The inner surface 13 of the fabric layer 12 is joined to the inner surface 17 of the electric heating/warming element 16 by adhesive 18.

In both of the implementations shown in FIGS. 1 and 1A, the fabric article 10 may further include a second fabric layer (not shown), with the heating/warming element and the barrier layer (if included) being interposed between the two fabric layers.

Referring to FIG. 1, 1A, and 2, in preferred implementations, the fabric layer 12 is made in any well known manner, e.g. the fabric layer 12 may be a knitted material, e.g., a plaited circular knitted or reverse plaited circular knitted material, or other circular knitted material (such as double knitted, single jersey knitted, two-end fleece knitted, three-end fleece knitted, terry knitted or double loop knitted material), or warp knitted or weft knitted material, or a woven or non-woven material. In applications where the fabric layer 12 of the fabric article 10 will be directed outwardly, away from the wearer's skin, the material of the fabric layer is preferably hydrophobic, in order to resist penetration of liquids. In other applications, where the fabric layer 12 of the fabric article 10 will be directed inwardly, toward the wearer's skin, the material of the fabric layer is preferably naturally hydrophilic, chemically rendered hydrophilic, or hydrophobic, in order to enhance removal and transport of perspiration away from the skin. The inner surface 13 of fabric layer 12, to which the adhesive 18 is adhered, is preferably flat. The exposed, outer surface 20 of fabric layer 12 may be flat or raised, e.g. by brushing, sanding or napping, and/or may be otherwise provided with decorative and functional features and finishes, e.g. as well known in the art.

Preferably, the barrier layer 14 is formed of a vapor permeable membrane which is nonporous hydrophilic or microporous hydrophobic or a combination of both, e.g. in layers, as appropriate to the nature of the intended use, or as otherwise desired. In certain implementations, it may also be preferred that the material of the barrier layer 14 be soft and stretchable. The barrier layer may be constructed and/or formulated to resist penetration of air and water droplets from passing through the composite fabric article 10 while being permeable to water vapor. In applications where it is desired that the fabric article 10 is stretchable, the fabric layer 12 may typically be a knitted material, and a preferred material for barrier layer 14 is poly urethane, e.g. as available from UCB Chemical Corp. of Drogenbos, Belgium, either micro-porous hydrophobic (preferred for use where the barrier layer 14 is directed outward) or nonporous hydrophilic (preferred for use where the barrier layer 14 is directed inward). Alternatively, in situations where relatively less stretch is required, e.g. in footwear, the fabric layer 12 may be a warp knitted material, and a preferred material for barrier layer 14 is poly tetrafluoroethylene (PTFE), e.g., as available from Tetratec, of Feasterville, Pa.

Figure 3:
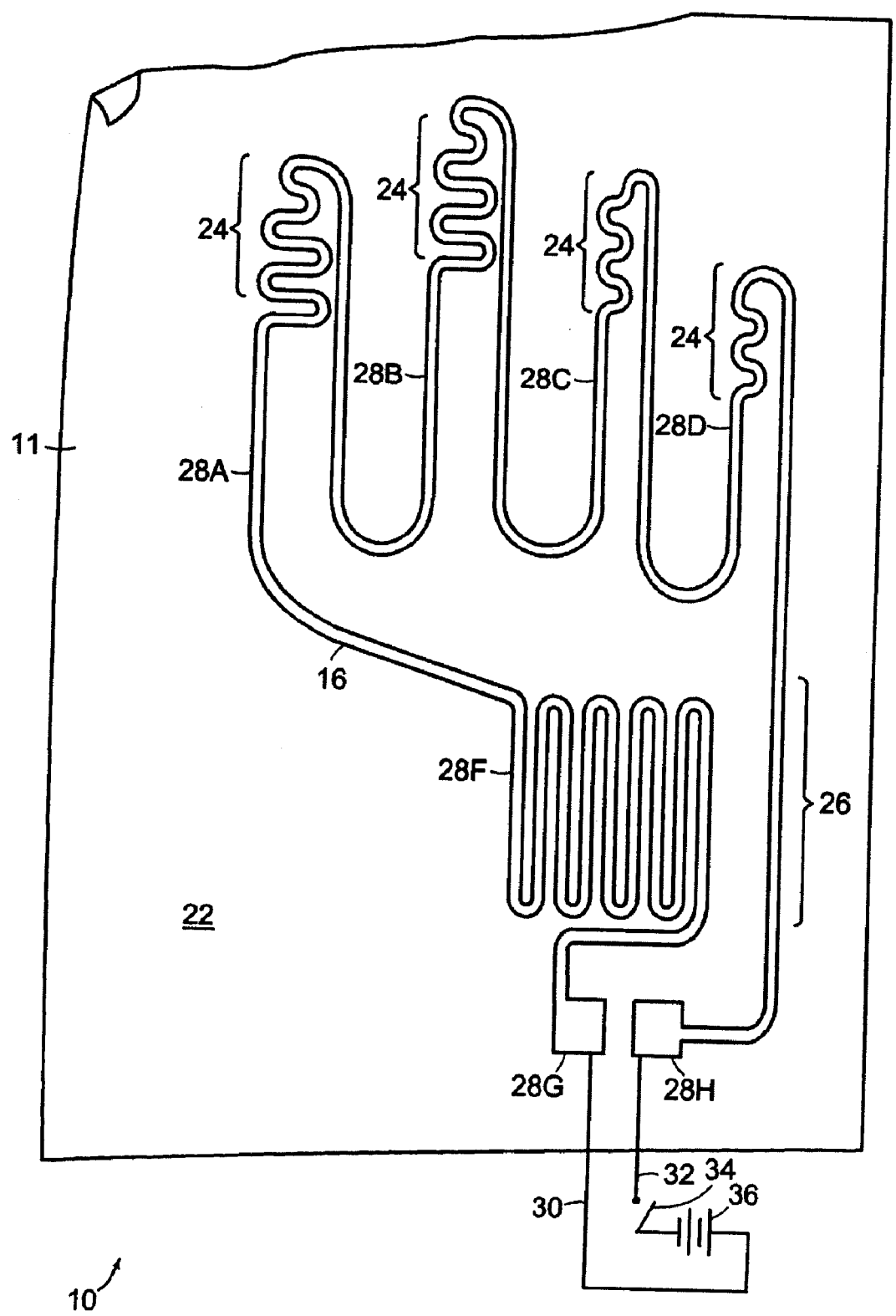
FIGS. 3, 4 and 5 are somewhat diagrammatic front plan views of the inner surfaces of heating/warming composite fabric articles of FIGS. 1 and 2, with electric heating/warming elements affixed thereupon, e.g., for a glove (FIG. 3), for an article of footwear (FIG. 4), and for a garment such as a shirt or jacket (FIG. 5)

The barrier layer 14 is joined to the inner surface 13 of fabric layer 12 by adhesive 18, typically applied in spots, lines or other discrete regions, or by attachment, lamination or other suitable manner of combining. A similar composite fabric (but having an additional internal fabric layer) is described in commonly assigned Lumb et al. U.S. Pat. No. 5,364,678, the entire disclosure of which is incorporated herein by reference. Referring also to FIG. 3, electric heating/warming element 16 is disposed upon the outer surface 22 of barrier layer 14.

In one implementation, the electric heating/warming element 16 is formed of metallized textile (including metallized textile fibers), or plastic sheeting or metal foil. Suitable metallized textiles are available, e.g., from Schlegel Systems Inc. of Rochester, N.Y. The textile may be metallized by any suitable technique, e.g., by metal coating, plating, or deposition, using chemical, electrical or mechanical techniques. The metal coating or deposit is made of a conductive material that provides a very low resistance, typically less than about 500 ohms per square. Examples of suitable conductive materials include silver, copper, nickel, nickel-chrome, and combinations of these metals. The metallized textile or plastic sheeting or metal foil can be produced in any desired electrically continuous (in whole or in part) circuit or produced in sheets and then die cut into the desired pattern. The element (or its parts) is then attached or inserted, e.g., alone or laminated to or between one or two layers of suitable non-conductive material, onto, or into, the fabric layer 12, to form a textile product. For a textile article in the form of a blanket, formation of the electric heating/warming element as a die cut stamping allows the buses to be formed integrally with the heating elements. The heating elements may be spaced asymmetrically so that selected regions get preferentially warmer than other regions, or, as described in more detail below, by providing selected heating elements or regions that have relatively less cross-sectional area, e.g. are relatively more narrow or otherwise have relatively greater resistance, than other heating elements or regions, for relatively greater localized generation of heat, can be provided to selected regions.

Alternatively, the heating/warming element may be formed of a conductive textile, e.g., a textile that includes conductive fibers and/or yarns. Suitable conductive fibers and yarns include, for example, carbon and polyaniline.

The predetermined pattern of the heating/warming element 16 may be custom designed for the particular purpose for which the composite fabric article 10 is to be used. For example, the pattern of the heating/warming element 16 of the composite fabric article 10 of FIG. 3 is designed for use in making a glove. For this purpose, the electric heating/warming element 16 forms a pattern having four elongated branches 28A, 28B, 28C, 28D (corresponding to fingers of a glove) and one or more sections 28F (corresponding to the palm or back of the body of a glove).

The heating/warming element 16 is formed as a continuous circuit, terminating at each end in a contact pad 28G, 28H, respectively. The contact pads preferably are disposed adjacent to each other in a region convenient for connection to a source of electrical current, e.g. for a glove, as shown, in a region to form the wrist of the glove. Still referring to FIG. 3, the heating/warming element 16 is connected, by wire conductors 30, 32 extending from contact pads 28G, 28H, respectively, in a circuit including a switch 34 and a power supply, e.g., a battery pack 36. When switch 34 is closed, the heating/warming element 16 is activated to generate heat/warmth.

The pattern features of the heating/warming element 16 shown in FIG. 3 are sized and shaped to conform to the regions of the resulting fabric article, i.e., the glove, so that the composite fabric can readily be cut to form one side of a glove. Patterns for use in other types and sizes of garments and fabric articles, e.g. such as socks, sweaters, jackets, shirts, pants, hats, gloves, footwear (e.g. shoes and boots) and so on, can be generated in a similar manner, e.g., as will be discussed below with reference to FIGS. 4-6.

Figure 4:
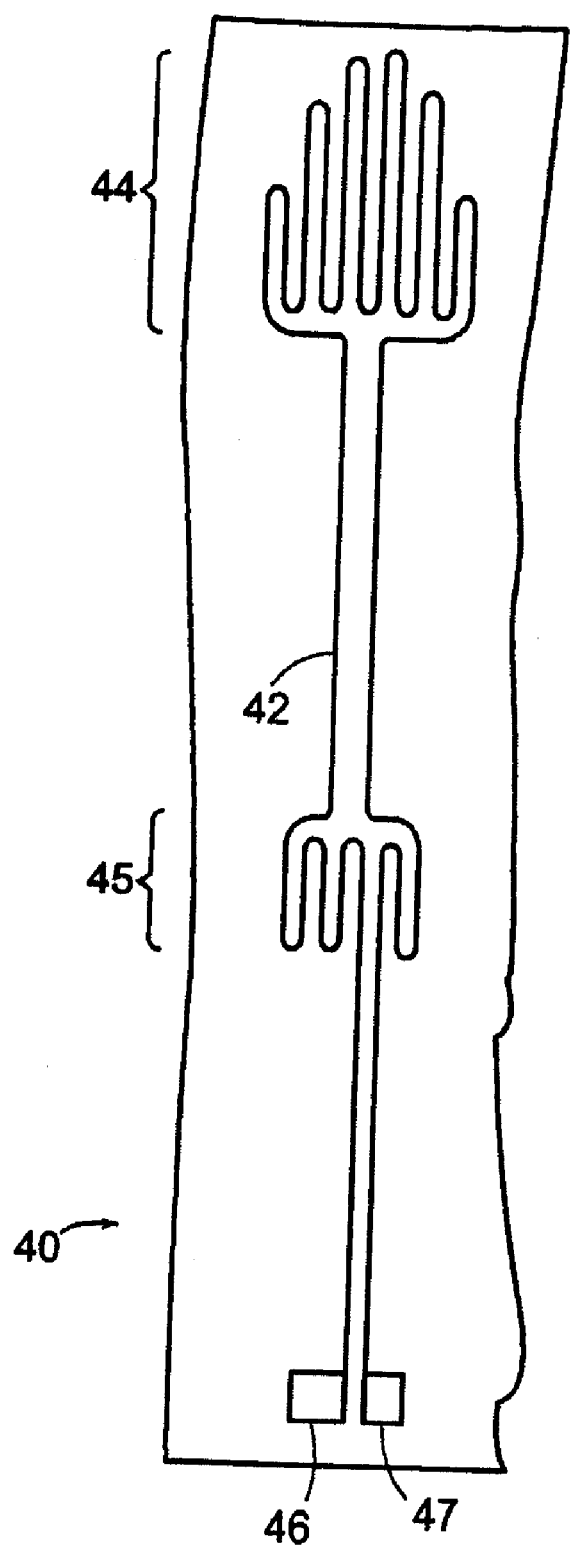

Referring to FIG. 4, a composite fabric article 40 has a heating/warming element 42 sized and shaped to conform to the regions of the selected resulting fabric article, i.e., in this implementation, a boot, to be heated/warmed so that the composite fabric can readily be cut to be formed and/or incorporated into a boot liner. In particular, the heating/warming element 42 has heating/warming regions 44, 45, with sections of relatively reduced cross-sectional area for increased resistivity and heat generation, corresponding to the toe/ball and heel surfaces, respectively, of a wearer's foot. The heating/warming element 42, which forms a circuit, terminates at each end in a contact pad 46, 47, respectively. The contacts pads are disposed adjacent to each other in a region convenient for connection to a source of power, e.g., as shown, in a region to extend into or above the ankle collar of the boot.

Figure 5:
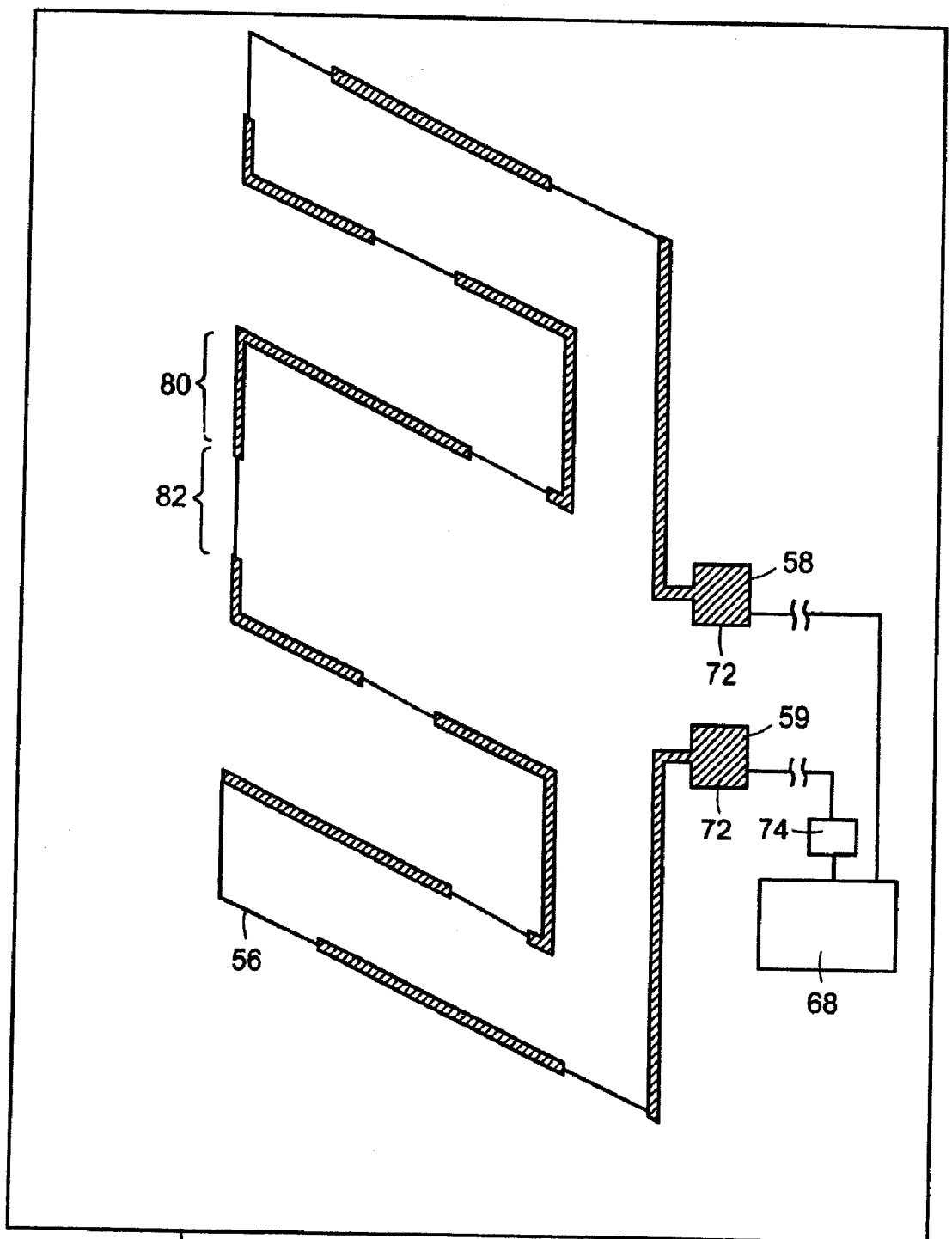

Referring to FIG. 5, a composite fabric article 50 has a heating/warming element 56 sized and shaped to conform to the regions of the selected resulting fabric article, i.e., in this implementation, the opposite chest surfaces of a garment such as a shirt or a jacket 60 (FIG. 6), to be heated/warmed. The heating/warming element 56 terminates at each end in a contact pad 58, 59, respectively, the pads being disposed adjacent to each other in a region convenient for connection to a source of power, as discussed below.

Figure 6:
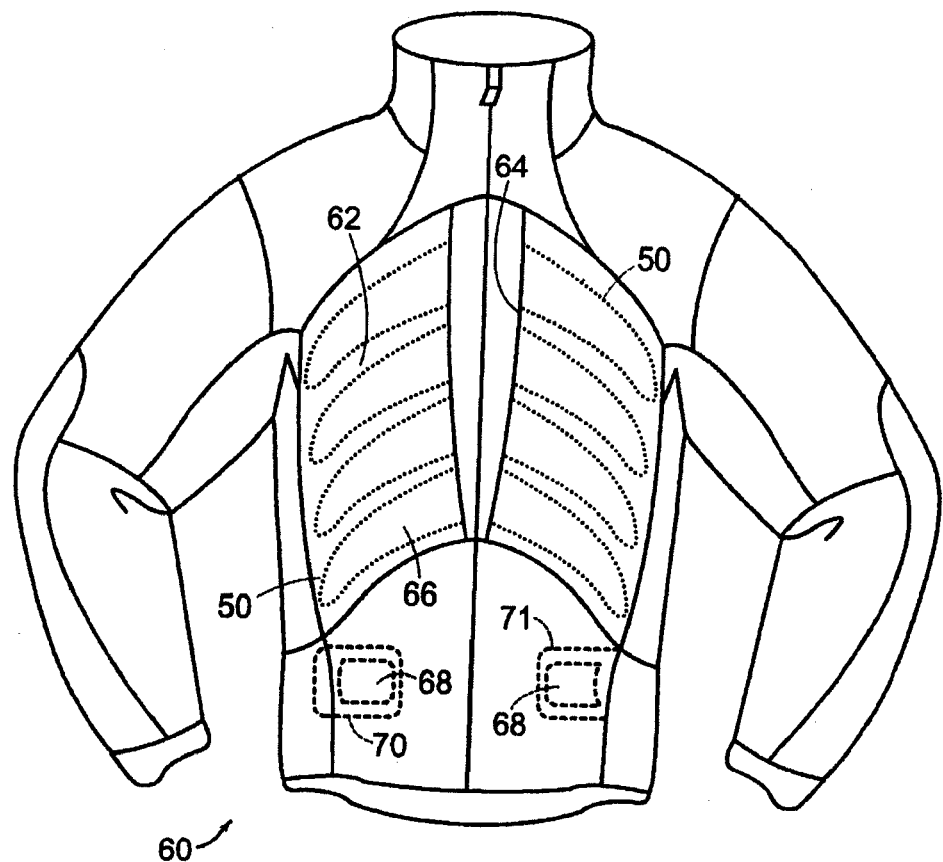
FIG. 6 is a somewhat diagrammatic front view of a garment, i.e., a jacket, incorporating the heating/warming composite fabric article of FIG. 5.

Referring also to FIG. 6, a pair of fabric articles 50 is shown incorporated into jacket 60. A battery pack 68 for powering each of the heating/warming composite fabric articles 50 is contained in the associated zippered pockets 70, 71. The battery pack 68, e.g. as available from Polaroid Corporation, of Cambridge, Mass., is preferably removably connected to the contact pads 58, 59 of heating/warming element 56 by releasable fastening elements 72, e.g. clips, snaps or other secure but releasable fastening elements. (The fastening elements may provide the electrical connection of the battery pack to the circuit, or, alternatively, may maintain the battery pack in position for contact of the battery pack with separate connectors.) This arrangement permits the battery pack 68 to be removed, e.g., whenever the fabric article 50 is to be washed, or for replacement or for recharging. The heating/warming circuit 56 may also include an oscillator chip 74 or other timing or cycling device for cycling application of electrical power from the battery pack 68 to the heating/warming element 56, e.g., to extend battery pack life. For example, a timing cycle of three minutes "on" followed by one minute "off" is considered suitable for an electric heating/warming composite fabric article 50 incorporated as a chest panel of the heating/warm jacket 60 suited for outdoors use.

In one preferred implementation, a composite fabric article 10 is formed by first combining the fabric layer 12 and barrier layer 14 with adhesive 18 disposed therebetween. An electric heating/warming element 16 is then affixed upon the surface 22 of the barrier layer 14. The resulting composite fabric article 10 is cut to shape, and otherwise processed using standard clothing procedures, for incorporation, e.g., into an article of clothing or the like. Alternatively, the heating/warming element 16 may be affixed upon the surface 22 of the barrier layer 14, before the barrier layer 14 and the fabric layer 12 are secured together.

Figure 7:
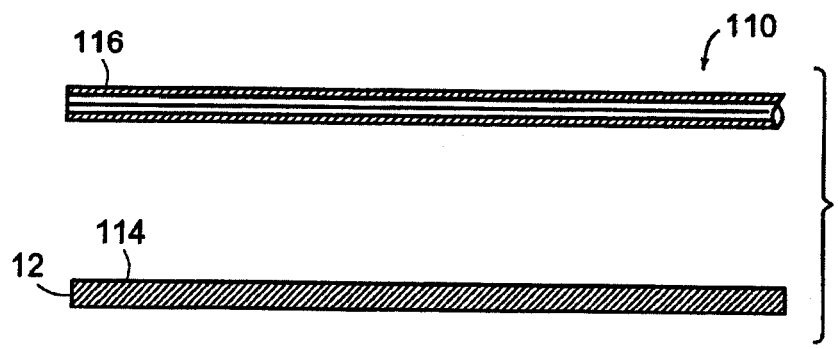
FIG. 7 is a somewhat diagrammatic exploded side edge view of components forming another implementation of a heating/warming composite fabric article constructed in accordance with the disclosure.
Figure 8:
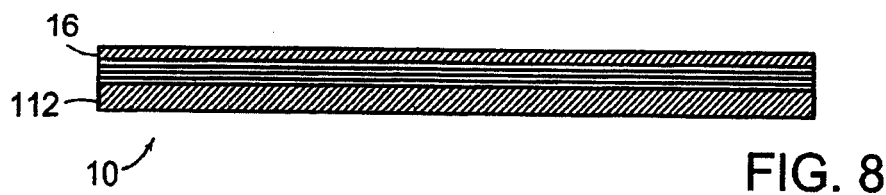
FIG. 8 is a somewhat diagrammatic side edge view of the heating/warming composite fabric article of FIG. 7.

Referring next to FIGS. 7 and 8, in another implementation, an electric heating/warming composite fabric article 110 consists of a fabric layer 112 having an inner surface 114 upon which an electric heating/warming element 116 is disposed.

In implementations where the heating/warming element 116 is affixed directly to the fabric layer 112, the composite fabric article 110 may be employed without a barrier layer. Alternatively, a pair of fabric articles 110 may be incorporated into a garment, e.g. a jacket 60, as shown in FIG. 6, where the outer coverings 62, 64 of the opposite chest surfaces of the jacket may be a shell material selected to provide a barrier layer overlaying the heating/warming composite fabric articles 110 incorporated into the jacket.

The relative amounts of heat/warmth generated by a region of an electrical heating/warming element in a composite heating/warming fabric article can be controlled, e.g., by varying the width and/or by varying the length and/or the thickness of a circuit element or segment, and/or by varying the conductivity/resistivity of the material forming a segment of the circuit element.

For example, referring to FIG. 5, a heating/warming element 56 formed of material of uniform conductivity and constant thickness has regions 80 and 82 of contrasting width, and, therefore, contrasting cross sectional area. As a result, in region 80 of relatively greater width, there is more conductivity, i.e. less resistance to current flow, and thus relatively less generation of heat/warmth. Similarly, in region 82 of relatively lesser width, there is less conductivity, i.e. more resistance to current flow, and thus relatively greater generation of heat/warmth. As a result, a composite heating/warming fabric article 50 can be designed with a circuit element 56 that delivers relatively greater amounts of heat/warmth to selected regions of the wearer's body.

Figure 9:
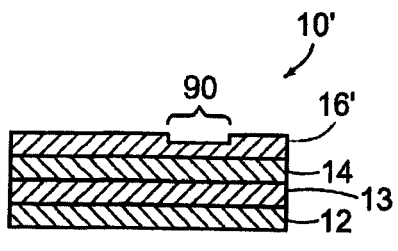
FIG. 9 is a somewhat diagrammatic side edge view of another implementation of a heating/warming composite fabric article constructed in accordance with the disclosure.

Alternatively, this effect may be obtained by applying a thinner layer of material, i.e., a region of relatively lesser cross sectional area. For example, referring to FIG. 9, a composite heating/warming fabric article 10' has a heating/warming element 16' having a region 90 of relatively lesser thickness (compared to adjacent regions).

Figure 10:
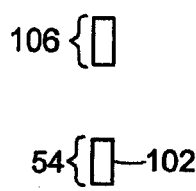
FIGS. 10 and 11 are sequential, somewhat diagrammatic front plan views of the inner surface of a heating/warming composite fabric article during construction in accordance with another implementation.
Figure 11:
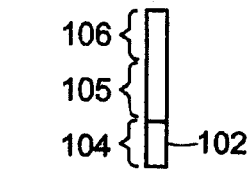

Alternatively, or in addition, a heating/warming element of constant dimension but with regions generating relatively different levels of heat/warmth may be formed by sequentially applying circuit regions using materials of inherently different conductivity. For example, referring first to FIG. 10, showing a composite heating/warming fabric article 100, a heating/warming element 102 is formed by affixing regions 104, 106 of a material of relatively greater conductivity, and thereafter, referring to FIG. 11, affixing region 108 of a material of relatively lower conductivity, region 108 interconnecting regions 104, 106.

These and other methods for adjusting the conductivity of electrical circuit regions may be employed alone, or in any desired combination.

The conductivity of various regions of the electrical circuit may be adjusted to suit the requirements of a particular application and thereby enhance wearer comfort. For example, in the case of gloves or footwear, heating the extremities (fingers and toes) is important to providing comfort, and generally the fingers and toes, especially at their tips, require more heating than the rest of the hands and feet. Thus, it is may be desirable to generate more heat in these specific areas, which may be accomplished in any of the manners discussed above.

Figure 15:
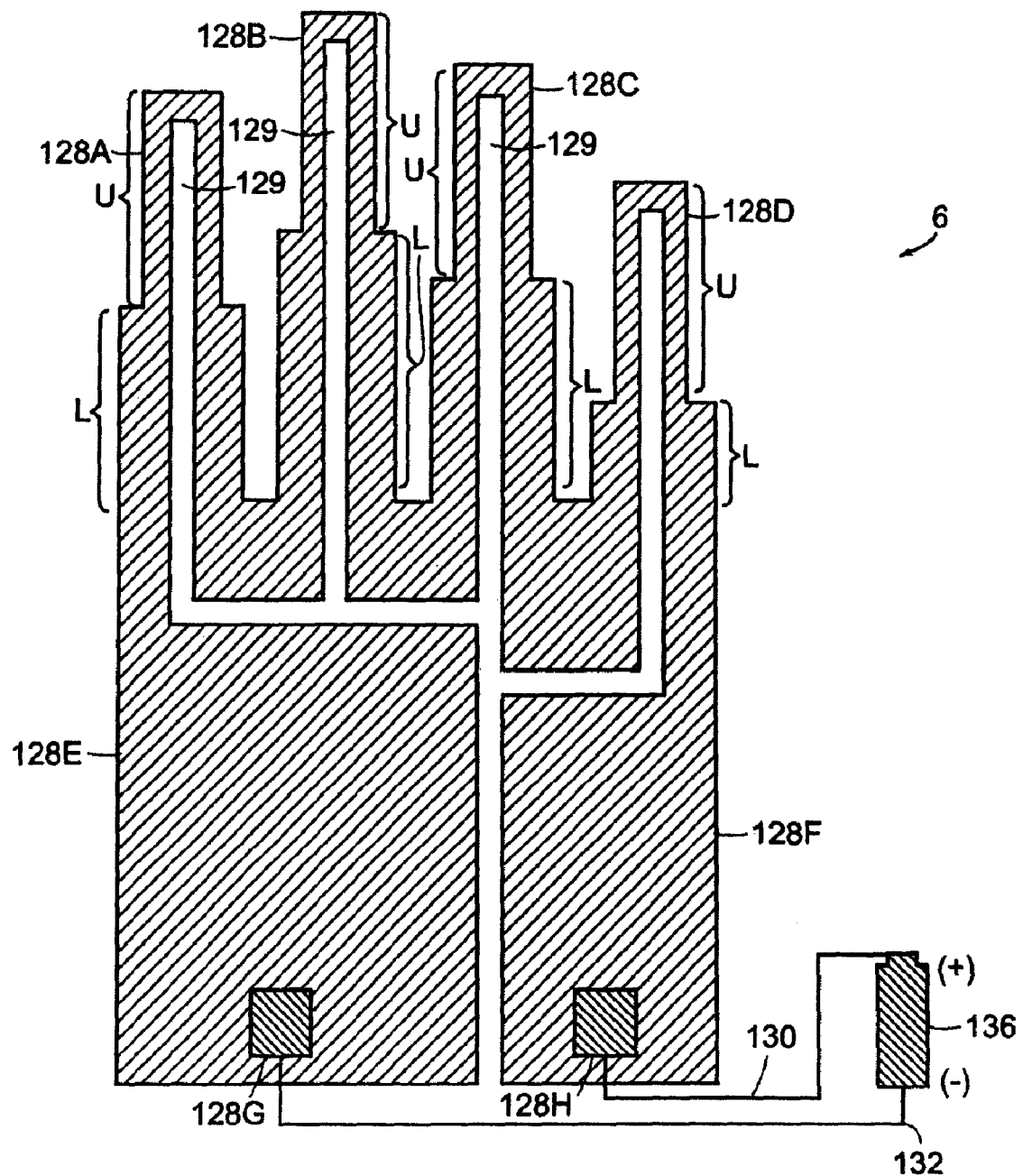
FIGS. 15-17 are somewhat diagrammatic front plan views of an electric heating/warming element for use in a glove.
Figure 16:
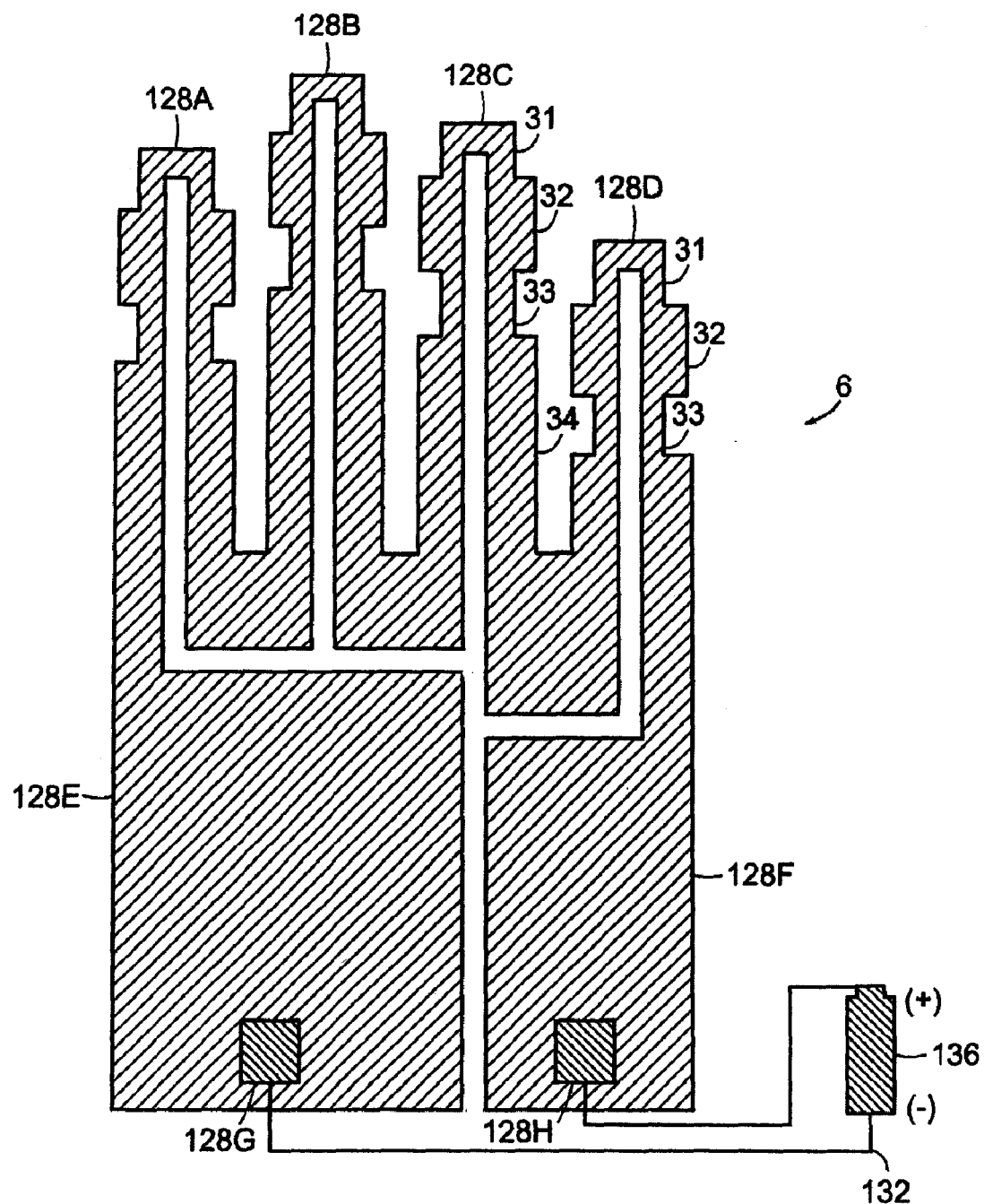

Preferred heating elements for use in gloves are shown in FIGS. 15 and 16. In both of these implementations, the electric heating/warming element 116 forms a pattern having four elongated branches 128A, 128B, 128C, 128D (corresponding to fingers of a glove) and sections 128E and 128F (corresponding to the palm or back of the body of a glove). A region 129 is cut out, or is not metallized, to reduce the effective area of the conductive material. The presence of region 129 increases the resistivity of the branches 128A-128D, while not significantly affecting the conductivity of the palm sections 128E and 128F. As a result, more heat will be generated in the branches 128A-128D than in the palm sections.

Additionally, within the branches 128A-128D there are regions of different width. For example, in the implementation shown in FIG. 15, the branches 128A-128D include upper regions, U, generally corresponding to the portion of the wearer's fingers from the first knuckle to the tip, and lower portions, L, generally corresponding to the portion of the wearer's fingers from the first knuckle to the intersection of the finger with the palm. The upper regions, U, are narrower than the lower regions, L, and thus have a greater resistivity and as a result generate more heat at the wearer's fingertips.

When the pattern shown in FIG. 15 is powered by 3.0 volts direct current source with an element having a resistance of 4.8 Ohms, the temperature generated in upper portions, U, is about 101° F. while the temperature generated in lower portions, L, is about 80° F. This provides greater heat generation in the fingers, and particularly at the tips of the fingers, providing more comfort for the user while conserving battery power.

Similarly, in the implementation shown in FIG. 16, the width of the branches 128A-128D is further varied, to provide relatively narrow areas 31 and 33, generally corresponding, respectively, to the tips and first knuckles of a wearer, and wide areas 32 and 34, generally corresponding to the areas between the knuckles of the wearer. In this example when the element is powered by a 3.0 volts direct current source with the element having a resistance of 4.8 ohms, the temperature generated at narrow areas 31 and 33 is about 101° F., while the temperature generated at wide areas 32 and 34 is about 80° F. The section next to the terminals and in the palm area will have very low resistance and thus will generate very little, if any, heat. Thus, the narrow areas 31 and 33 provide high heat generation at the fingertips and close to the arteries (at the first knuckle). Providing heat generation at regions close to arteries helps to warm the blood and improve circulation. As a result, the user's fingers are kept warm without overheating the rest of the user's hand, while also conserving battery power.

In some instances, heat can be provided to a user's extremities by providing heat to a region through which a large volume of blood supply flows. For example, heat can be provided through a user's skin and into the user's bloodstream at a vascular surface location defined as an area where a major blood vessel or vessels larger than capillaries pass sufficiently near the skin surface that heat may be conducted directly from the surface of the skin into the blood flowing through the major blood vessel or vessels toward a body extremity. Thus, the heated blood supply is then circulated to the user's extremities, resulting in warmer extremities.

Figure 17:
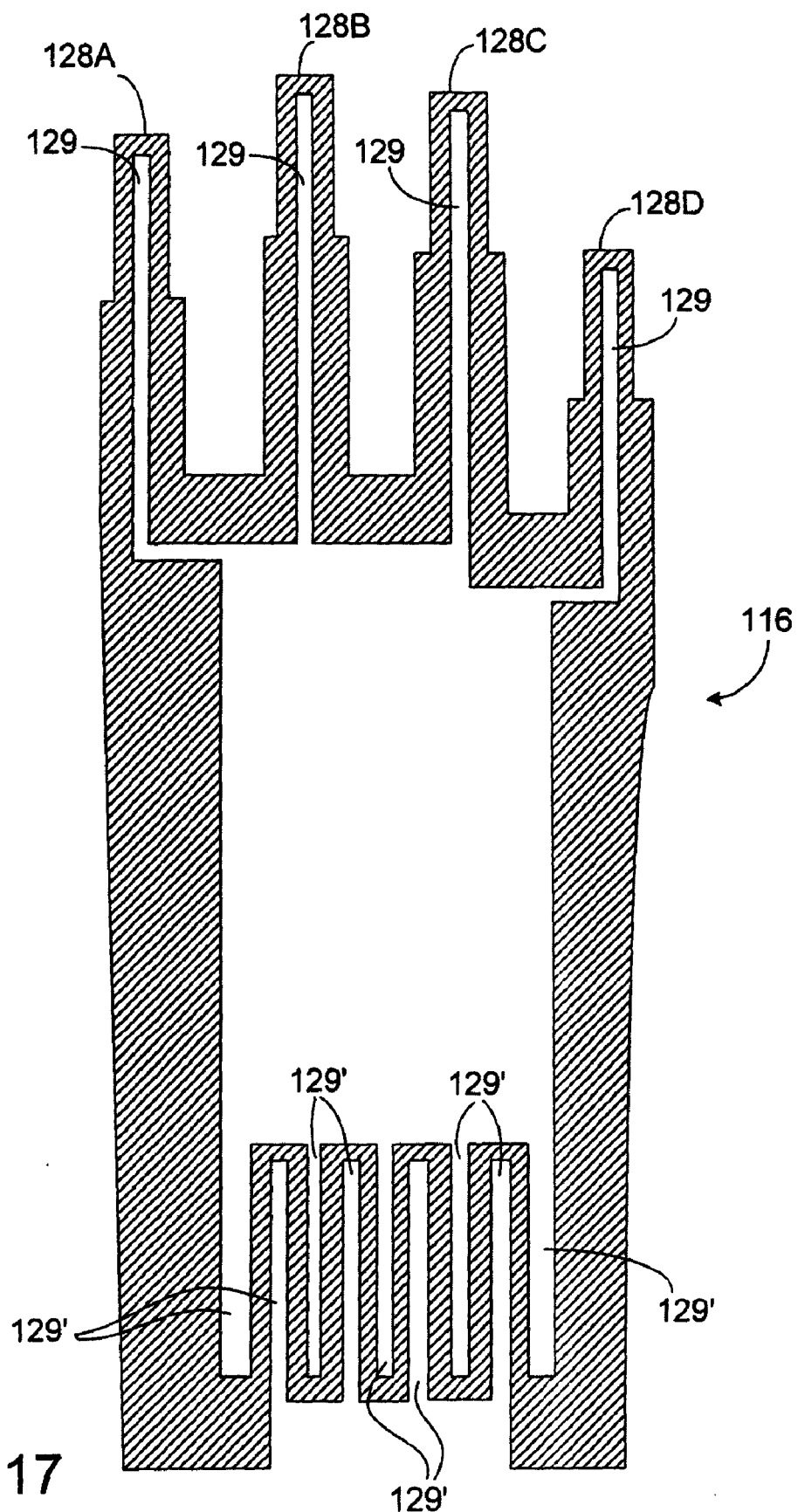

Referring to FIG. 17, the electric heating/warming element 116 forms a pattern having four elongated branches 128A, 128B, 128C, 128D (corresponding to fingers of a glove) placed in a manner similar to that depicted in FIG. 15. As discussed above, the presence of region 129 in the elongated branches increases the resistivity of the fabric article in the elongated branches. Similarly to region 129, a region 129' is not metallized, which reduces the effective area of the conductive material, and increases the resistivity in the corresponding portion of the fabric article. Region 129' is positioned to cover the wrist of the user, where a substantial blood supply flows towards the elongated branches through major blood vessels, so the blood is heated as it passes through the wrist and towards the user's fingers. Accordingly, blood is heated both at the wrists, as it flows to the fingers and fingertips, and directly at the fingers and fingertips.

Figure 12:
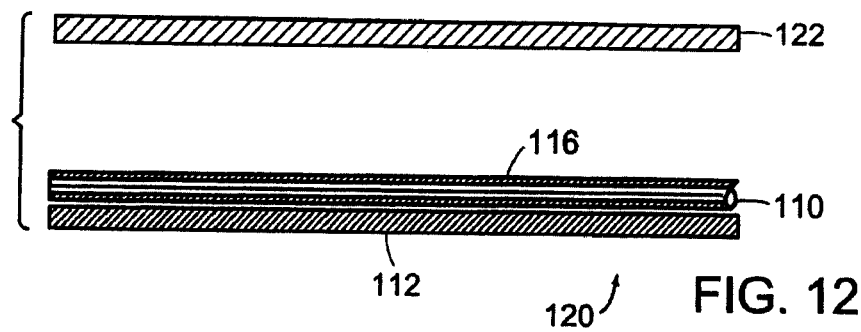
Figure 13:
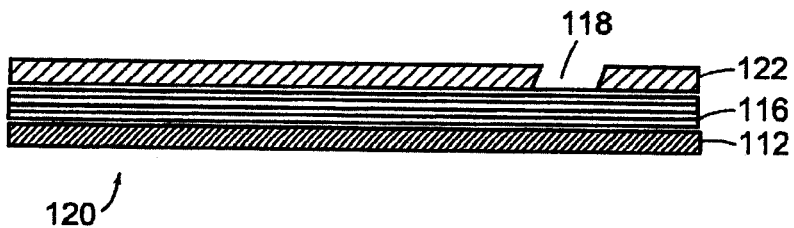
FIGS. 13 and 14 are somewhat diagrammatic side edge views of alternate implementations of the heating/warming composite fabric article of FIG. 12.
Figure 14:
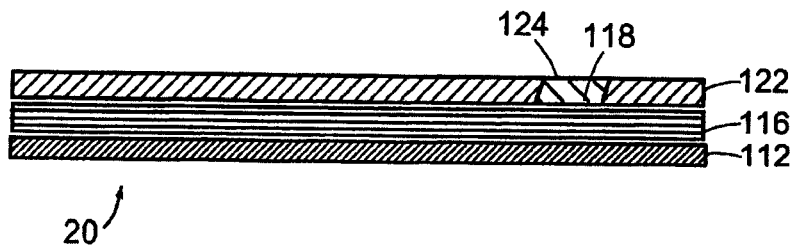

In the implementations shown in FIGS. 15, 16, and 17, power is delivered to the circuit in the same manner as discussed above with reference to FIG. 3. That is, the heating/warming element 16 is formed as a continuous circuit, terminating at each end in a contact pad 128G, 128H, respectively, for connection to a source of power, e.g., a battery pack 136, by wire connectors 130, 132. In yet another implementation, the electric heating/warming composite fabric article 110 described above with reference to FIGS. 5 and 6 may be further processed. For example, referring now to FIGS. 12, 13 and 14, in an electric heating/warming composite fabric article 120, a barrier layer 122, e.g. as described above, is attached adjacent to the side of the inner surface 114 of the fabric layer, overlying at least a portion of the heating/warming element 116, e.g. using adhesive, also as described above. Preferably, contact pads 118 (only one is shown) of heating/warming element 116 are left exposed for connection to a source of power (FIG. 13), or electrical connectors 124 (only one is shown) are provided for connecting the contact pads and power source through the barrier layer 122 (FIG. 14).

In cases described above, the heating/warming element is supported by a fabric layer, whether or not a barrier layer is provided. The fabric layer may be naturally hydrophilic, chemically rendered hydrophilic, or hydrophobic. In some preferred implementations, a barrier layer is provided at least adjacent to the inner surface of the fabric layer, i.e., attached to the fabric layer (with or without intervening materials) or spaced from attachment to or upon the fabric layer, but positioned at the inner surface side of the fabric.

A barrier layer associated with or attached, e.g. by lamination or other techniques, onto the surface of the fabric layer 12 upon which the heating/warming element 16 is affixed (e.g. barrier layers 62, 64, FIG. 6; and barrier layer 122, FIGS. 12-14, respectively) serves also to protect the circuit against the effects of abrasion that might otherwise deteriorate the quality or continuity of the electrical heating circuit. The barrier layer also serves to resist short-circuiting in the event condensate forms on the fabric layer inner surface. The barrier layer may be formed of any suitable, protective thermoplastic material. It will preferably be micro porous hydrophobic or nonporous hydrophilic if it is a complete layer. Where a complete layer is not desired or employed, the barrier layer may be applied exclusively to the region of the printed circuit itself, in which case, it will preferably be nonporous hydrophobic.

It has also been discovered that electrically conductive heating/warming circuits for use in fabric articles subject to physical stress of repeated crushing, bending and flexing during use, including articles such as garments, including footwear, sock, gloves, etc., home textiles, accessories, etc., may suffer from decay in resistivity performance, resulting, e.g., in gradual increase in resistance over localized regions. Therefore, in another implementation, conductive metallized textile, e.g. in the form of metallized woven fabric material, configured into an electrically conductive heating/warming circuit by cutting in a suitable fashion, e.g. by laser cutting, die cutting, stamping, manual cutting, etc., is at least partially impregnated with a suitable thermoplastic material, to resist and reduce the effects of repeated physical crushing, bending and flexing during use.

Figure 18:
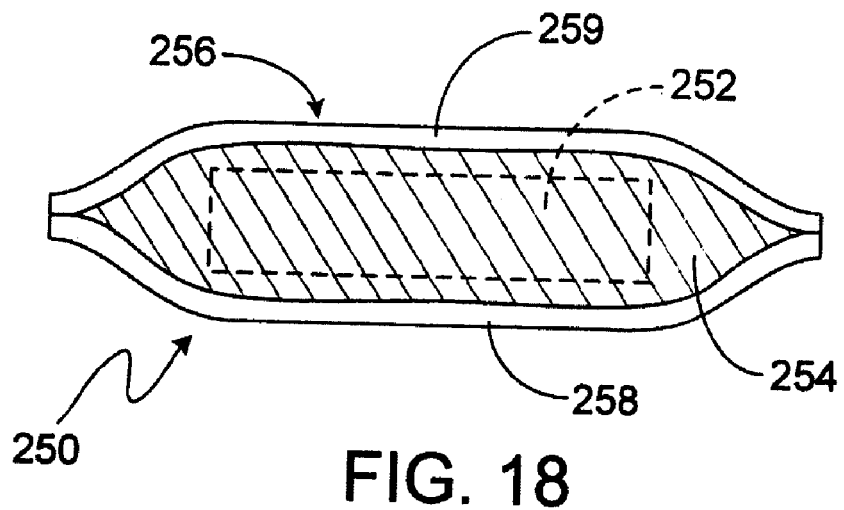
FIG. 18 is a somewhat diagrammatic end view of an electric heating/warming element consisting of a woven fabric laminate incorporating an electrically conductive metallized textile at least partially impregnated with a suitable thermoplastic polymeric material.

Referring to FIG. 18, in one exemplary implementation, a laminated electric heating/warming element 250 consists of a circuit element 252 formed of conductive metallized woven fibers, formed, e.g., of suitable synthetic material such as nylon or polyester, at least partially impregnated by a suitable synthetic material 254 applied in the form, e.g., of an adhesive, a hot melt adhesive, or a melted film, and incorporated in a fabric laminate 256 formed of two layers of woven fabric 258, 259. The woven fabric selected for use in the laminated electric heating/warming element 250 is preferably a relatively lightweight fabric woven in both warp and fill directions to make the woven fabric very stable.

Testing of the improved laminated electric heating/warming element 250 has shown that increase in resistance is typically limited to about 10 percent, as compared to increases of several hundred percent experienced with standard electric heating/warming elements (without at least partial impregnation) under similar testing conditions.

Figure 19:
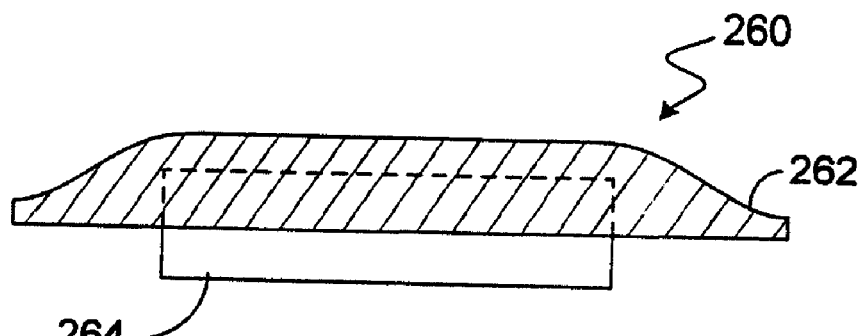
FIGS. 19 and 19A are similar diagrammatic end views of electric heating/warming elements, each consisting of a composite element including an electrically conductive metallized textile at least partially impregnated with a suitable thermoplastic polymeric material from two opposed sheets of barrier film or a single sheet of thermoplastic polymeric barrier material film, respectively, disposed adjacent the metallized thermoplastic barrier material and exposed to conditions of heat and temperature.
Figure 19A:
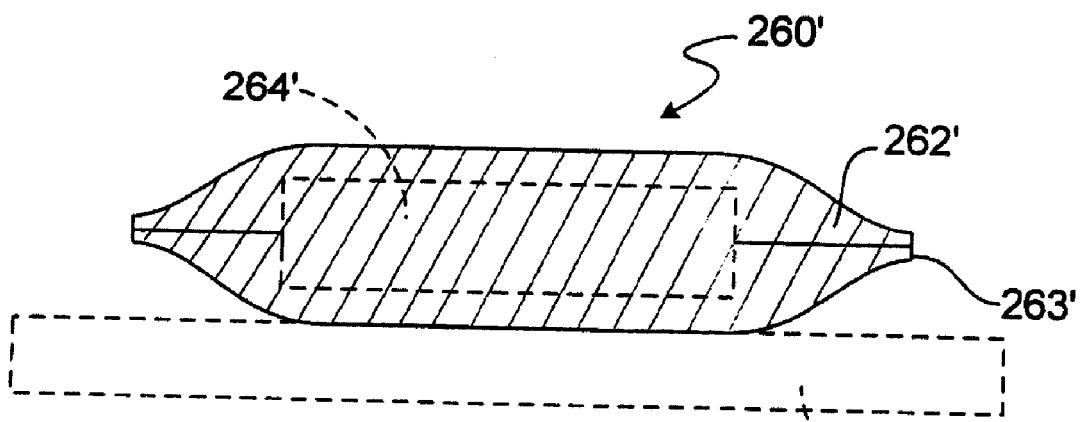

Referring now to FIGS. 19 and 19A, in other implementations, a composite electric heating/warming elements 260, 260', respectively, are formed of thermoplastic barrier film, e.g. polyurethane, or any suitable polymer, copolymer or block polymer, disposed at one surface (film 262; FIG. 19), or, more preferably, at both surfaces (films is 262', 263'; FIG. 19A) of a heating/warming circuit element 264, 264', respectively, configured of conductive metallized woven fibers, formed, e.g., of suitable synthetic material, such as nylon or polyester.

By way of example, and with reference to FIG. 19A, an electric heating/warming circuit element 264' is disposed between opposed layers of thermoplastic barrier material 262', 263', e.g. polyurethane film 6 mil (0.006 inch) thick, forming a sandwich. In one implementation, the sandwich is subjected to heating at about 350° F. and pressure of about 7 psi (pounds per square inch) for about 50 seconds. The polyurethane material is observed to flow into and through the metallized, woven conductive fibers of the electric heating/warming circuit material to create an electric heating/warming element in which the heating/warming circuit element is at least partially impregnated by the polyurethane material of the barrier. The resulting composite electric heating/warming element has an overall thickness of about 2 mil (0.002 inch).

In FIG. 19, a composite electric heating/warming element 260, formed by at least partial impregnation of an electric heating/warming circuit element 264 by a single layer of thermoplastic barrier material 262 is shown.

In all three implementations, the impregnating material provides good air-and-water-droplet resistance, and protection for the heating/warming circuit element in rainy conditions and wet environments. The impregnated unit can be laminated with woven fabric at one or both surfaces. Also, in some implementations, a breathable thermoplastic barrier material may be employed to allow moisture vapor, i.e. sweat vapor, to pass through the barrier material for increased wearer comfort.

Also, as described above, both the laminated electric heating/warming element 250 and the composite electric heating/warming elements 260, 260' may thereafter be attached upon or associated with one surface or both surfaces of a fabric article, F (suggested in dashed line in FIG. 19A), including, e.g., garments, such as gloves, footwear, socks, apparel and apparel accessories, sleeping bags, heating pads for medical treatment and pain management, and the like.

Figure 20:
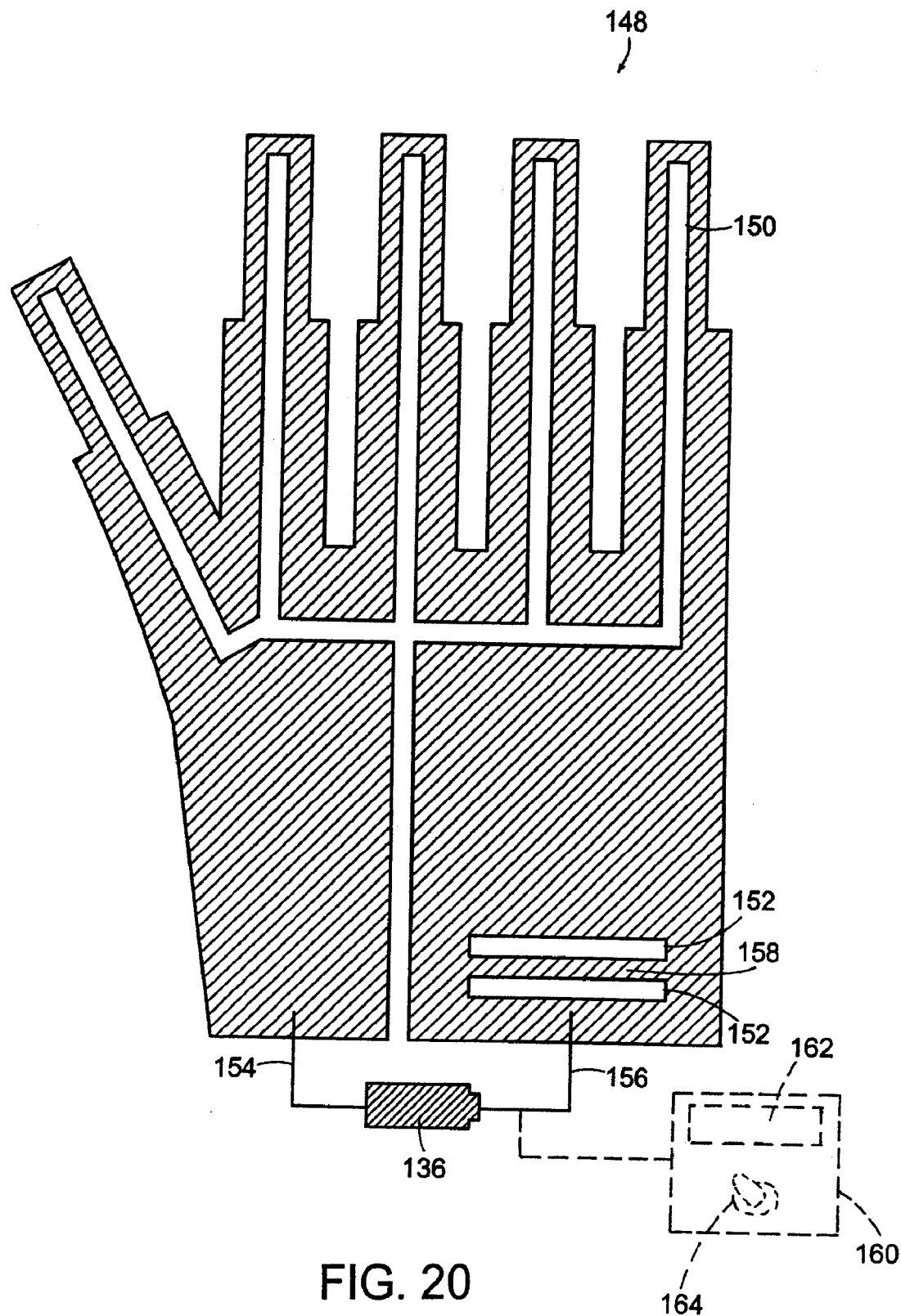
FIG. 20 is a somewhat diagrammatic front plan view of an electric heating/warming element for use in a glove, including a temperature sensing element.

Also, if desired, the temperature of a portion of the heating/warming element can be measured during use. For instance, a sensor can be included to determine the temperature at the fingertip of the glove. The sensor can be placed at the fingertip, with conductive lead running down the finger. However, this may interfere with dexterity, and thus it may be desirable to simulate the fingertip temperature at another, alternative area of the glove and measure the temperature at that alternative area. For example, in the heating/warming element 148 shown in FIG. 20, the temperature at fingertip 150 can be simulated by providing two cut-out areas 152 in the palm region, near the conductors 154, 156, that define a rectangular area 158 calculated to have the same resistance as the portion of the circuit in the fingertip 150. Thus, the temperature at the fingertip can be estimated remotely by measuring the temperature of the area 158. This temperature data can be monitored, in conjunction with a controller 160, e.g., a voltage regulator, to automatically shut off the battery or deliver less power to the circuit when a maximum temperature is detected, and to turn on the battery or increase power delivery when a minimum temperature is detected. Alternatively, or in addition, the temperature can be displayed on a read-out 162, e.g. mounted on the glove. A manual control 164 can also be provided, to allow the wearer to turn the battery on and off or to adjust the temperature.

A number of implementations have been described. Nevertheless, it will be understood that various modifications may be made without departing from the spirit and scope of this disclosure.

Figure 21:
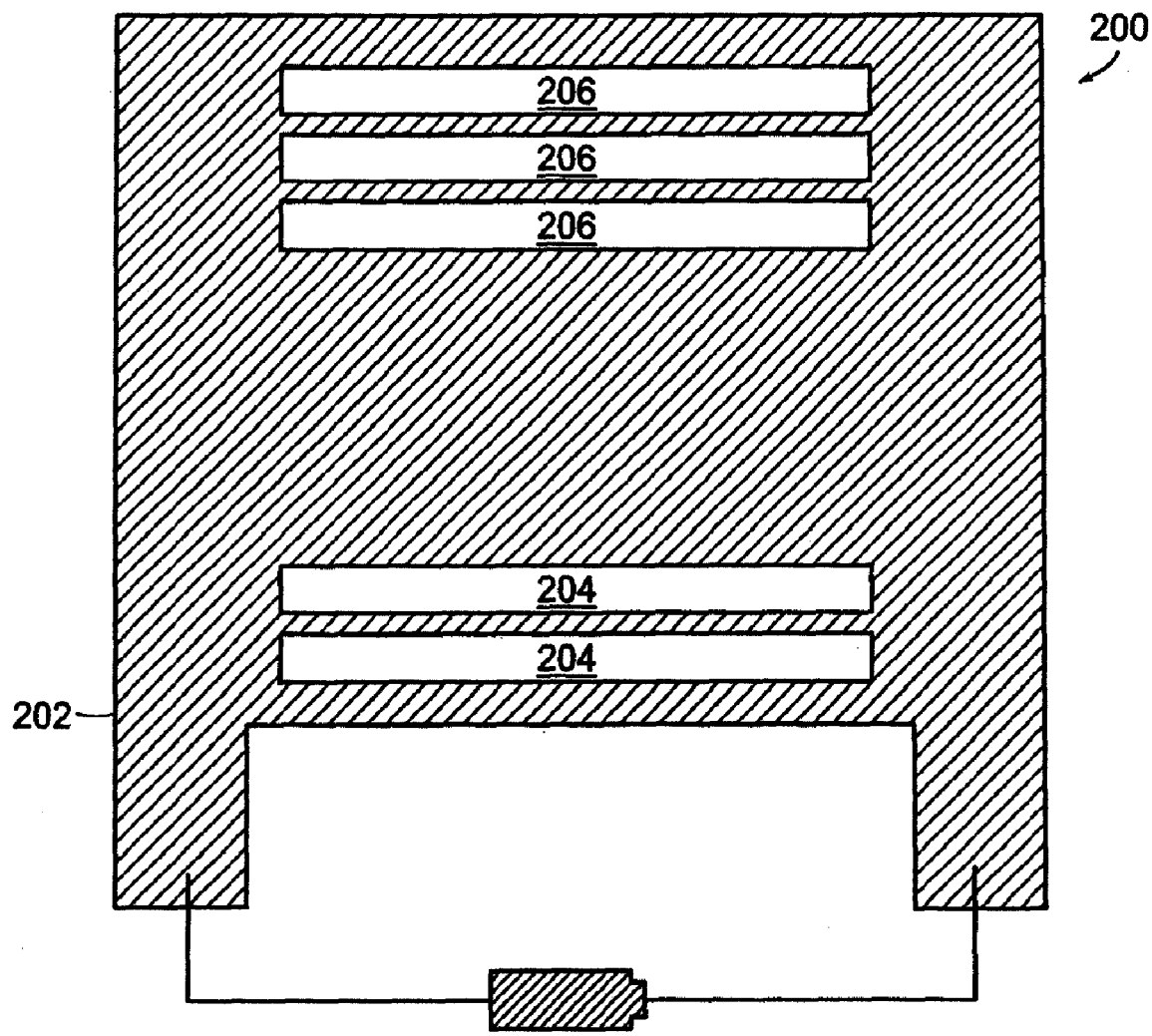
FIG. 21 is a somewhat diagrammatic front plan view of an electric heating/warming element that includes a parallel circuit.

For example, additional fabric layers may be added to enhance various aesthetic and functional characteristics of the electric heating/warming composite fabric article. Moreover, while the circuits in the implementations discussed above have been series circuits, the circuit used in the heating/warming element may be a parallel circuit, e.g., as shown in FIG. 21. In the heating/warming element 200, shown in FIG. 21, the relatively wide areas 202 act as buses, while the cut-out areas 204, 206 provide areas of higher resistivity, as discussed above. The circuit shown in FIG. 21 also illustrates that the circuit need not be symmetrical, e.g., in the circuit shown in FIG. 21, there are three cut-out areas 206 in the upper region of the circuit, but only two cut-out areas 204 in the lower region of the circuit. Also, the buses may be formed integrally with the heating elements, as described above, or may be formed separately and joined or otherwise suitably placed in electrical communication.

Figure 22:
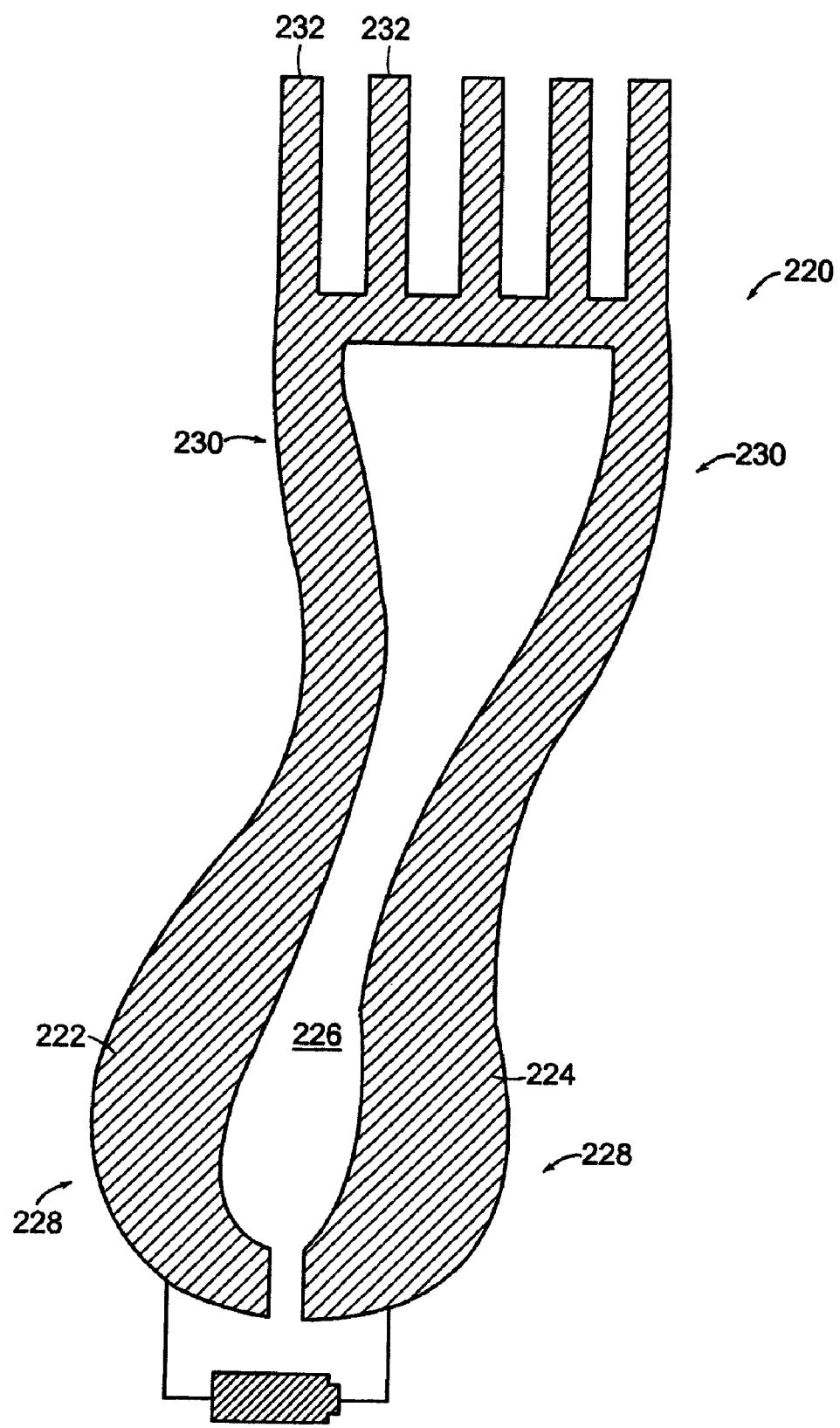
FIG. 22 is a somewhat diagrammatic front plan view of an electric heating/warming element for use in an article of footwear.

Furthermore, while circuits for gloves have been described above, by way of example, the heating/warming element may be used a large variety of other applications, including garment and home textile applications. For example, a heating/warming element 220, for use in a sock, shoe, or other article of footwear, is shown in FIG. 22. In the heating/warming element 220, the circuit includes a left hand portion 222 and a right hand portion 224, separated by a cut-out area 226. Cut-out area 226 is shaped to provide relatively wide bus areas 228 in the heel region, and relatively narrower, higher resistivity areas 230 in the forefoot region. The toe portions 232 are narrowest of all, and thus have the highest resistivity, so that the highest temperature will be generated adjacent the wearer's toes. Also, although die cut materials are described, other means can also be used to cut or shape the conductive fabric, e.g., the fabric can also be laser cut or cut using ultra sound.

Figure 23:
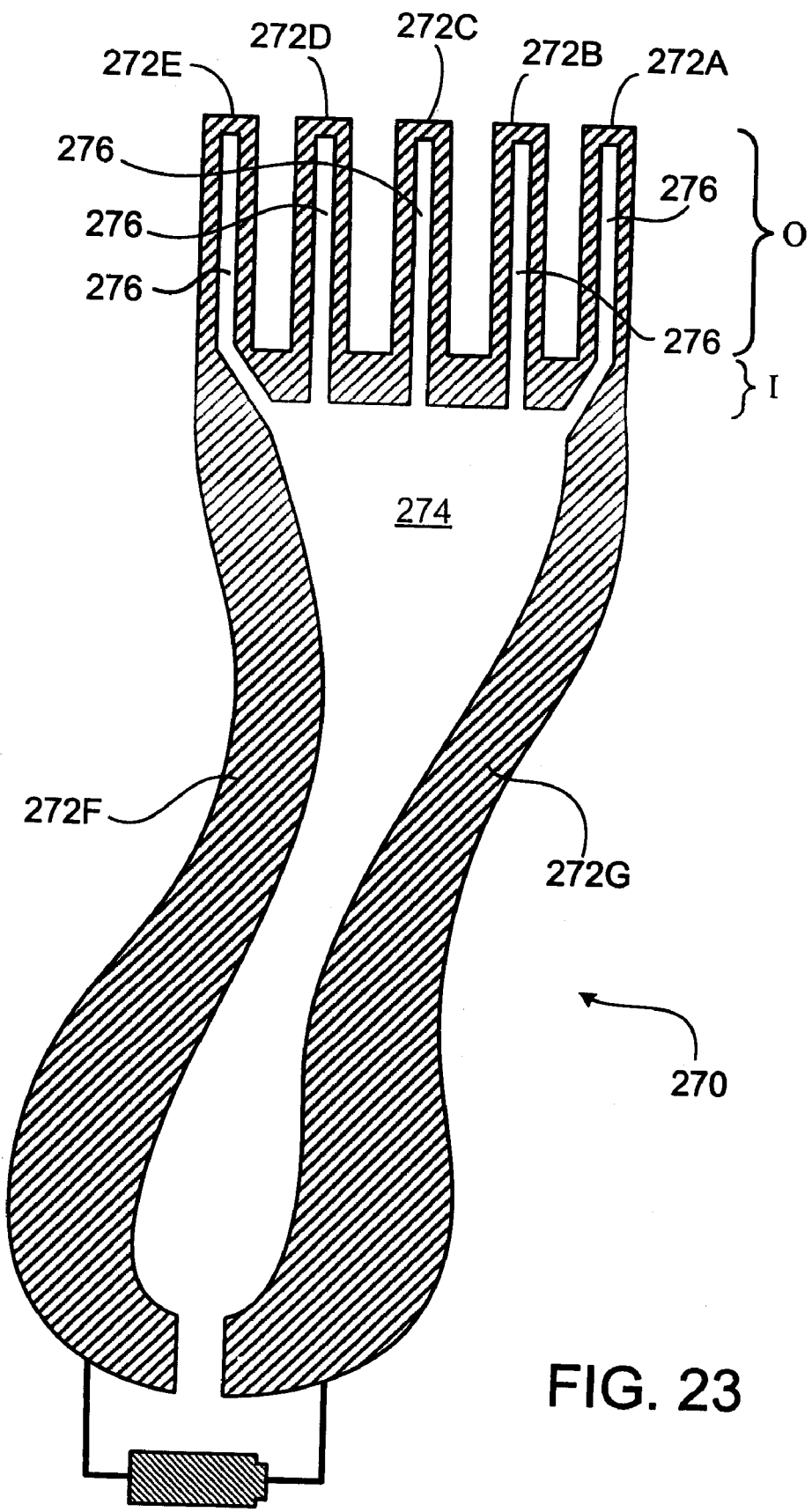
FIG. 23 is a somewhat diagrammatic front plan view of another electric heating/warming element for use in an article of footwear.

A preferred heating element for use in footwear is shown in FIG. 23. In this implementation, the electric heating/warming element 270 forms a pattern having five elongated branches 272A, 272B, 272C, 272D, 272E (corresponding to a wearer's toes, e.g. in a sock) and sections 272F and 272G (corresponding to the arch and heel regions of the body of a sock, sock liner, shoe, boot or other footwear element). A region 274 is cut out, or is not metallized, to reduce the effective area of the conductive material. The presence of regions 276 increases the resistivity of the toe branches 272A-272E, while not significantly affecting the conductivity of the foot sections 272F and 272G. As a result, more heat will be generated in the toe branches 272A-272E than in the foot sections. Additionally, generally within the branches 272A-272E there are regions of different width. For example, the toe branches 272A-272E include upper regions, O, generally corresponding to the portion of the wearer's toes, and inner portions, I, generally corresponding to the footpad portion of the wearer's foot, at the base of the toes. The outer regions, O, are narrower than the inner regions, I, and thus have a greater resistivity and as a result generate more heat at the wearer's toes.

When the pattern shown in FIG. 23 is powered by 3.6 volts direct current source (e.g. a Lithium-ion battery) with an element having a resistance of 3.6 Ohms, the temperature generated in outer portions, O, is about 130° F. while the temperature generated in inner portions, I, is about 80° F. This provides greater heat generation for the toes, and particularly at the tips of the toes, providing more comfort for the user while conserving battery power.

Also, in the laminated and composite heating/warming element at least partially impregnated with thermoplastic film, should a partial break or tear occur in the electrical circuit formed by the conductive, metallized woven fabric, overheating (or, in more extreme conditions of a tear, arcing) may occur in the break region while the circuit is connected to a power source. The generation of heat due to overheating or arcing will cause the opposed edges of the metallized woven fabric to melt and recede from each other. The electric heating/warming element with thus perform in the manner of an active fuse to interrupt flow of current through the electrical circuit.

Figure 24:
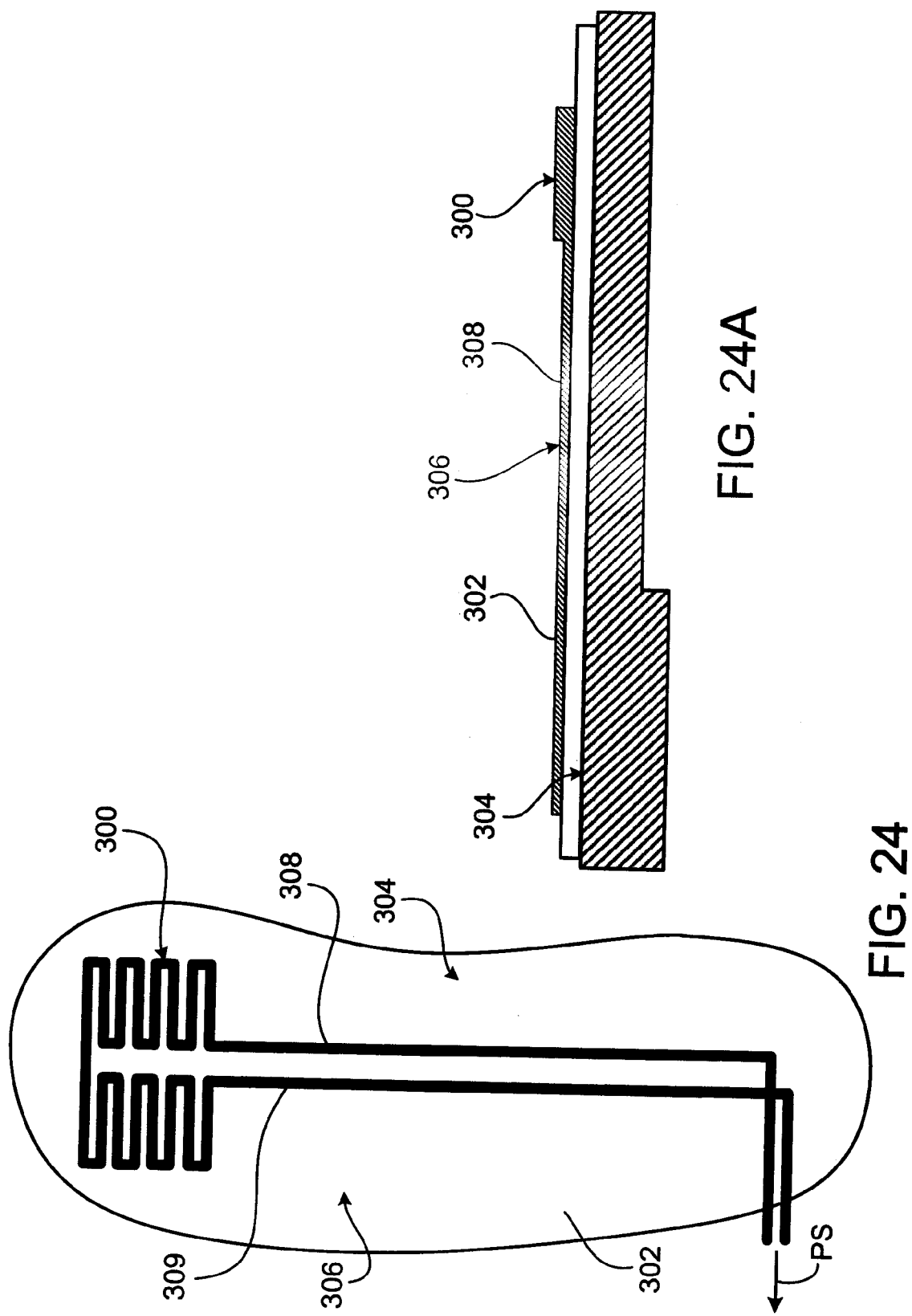
Figure 25:
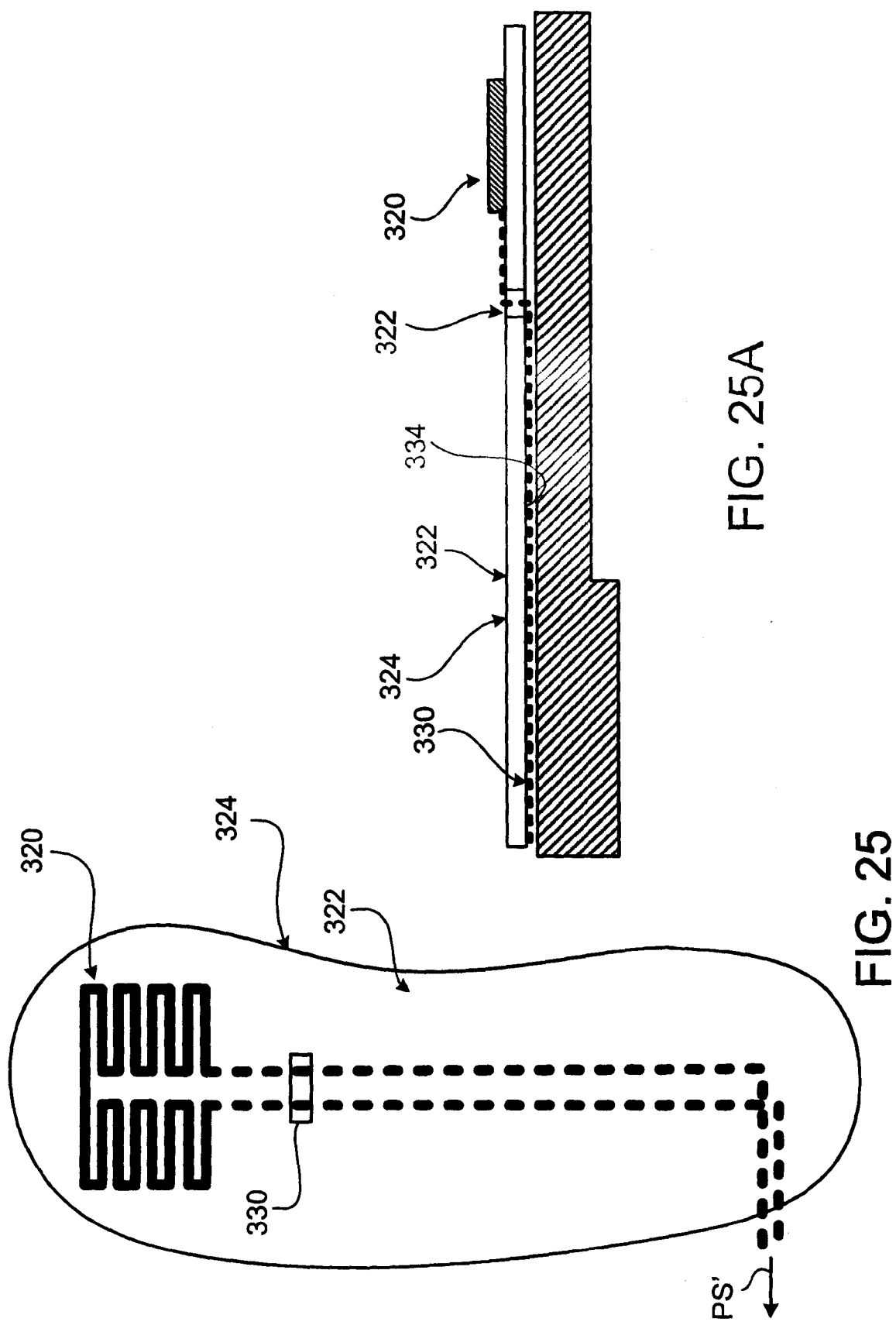

Referring next to FIGS. 24 and 24A, an electric heating/warming element 300, e.g. generally as described above with reference to FIG. 23, may be adhered to the top surface 302 of a shoe insert 304, e.g. with a covering of shoe lining fabric 306 ("cambrelle") on top of the heating element to provide additional protection against abrasion. The heating element 300, mounted at the forward surface of the shoe insert 304, is connected to a power supply (indicated by arrow, PS), e.g., by two narrow strips of copper 308, 309 laminated between opposed sheets of film. In another implementation, shown in FIGS. 25 and 25A, an electric heating/warming element 320, e.g. generally as described immediately above, is adhered to the top surface 322 of shoe insert 324. The heating element 320 is mounted at the forward surface of the shoe insert 324 and connected to a power supply (indicated by arrow, PS') by a bus 330, which may be inserted into a longitudinal slit 332 in the shoe insert, as shown, or alternatively may be disposed along the bottom side surface 334 of the shoe insert 324.

Figure 26:
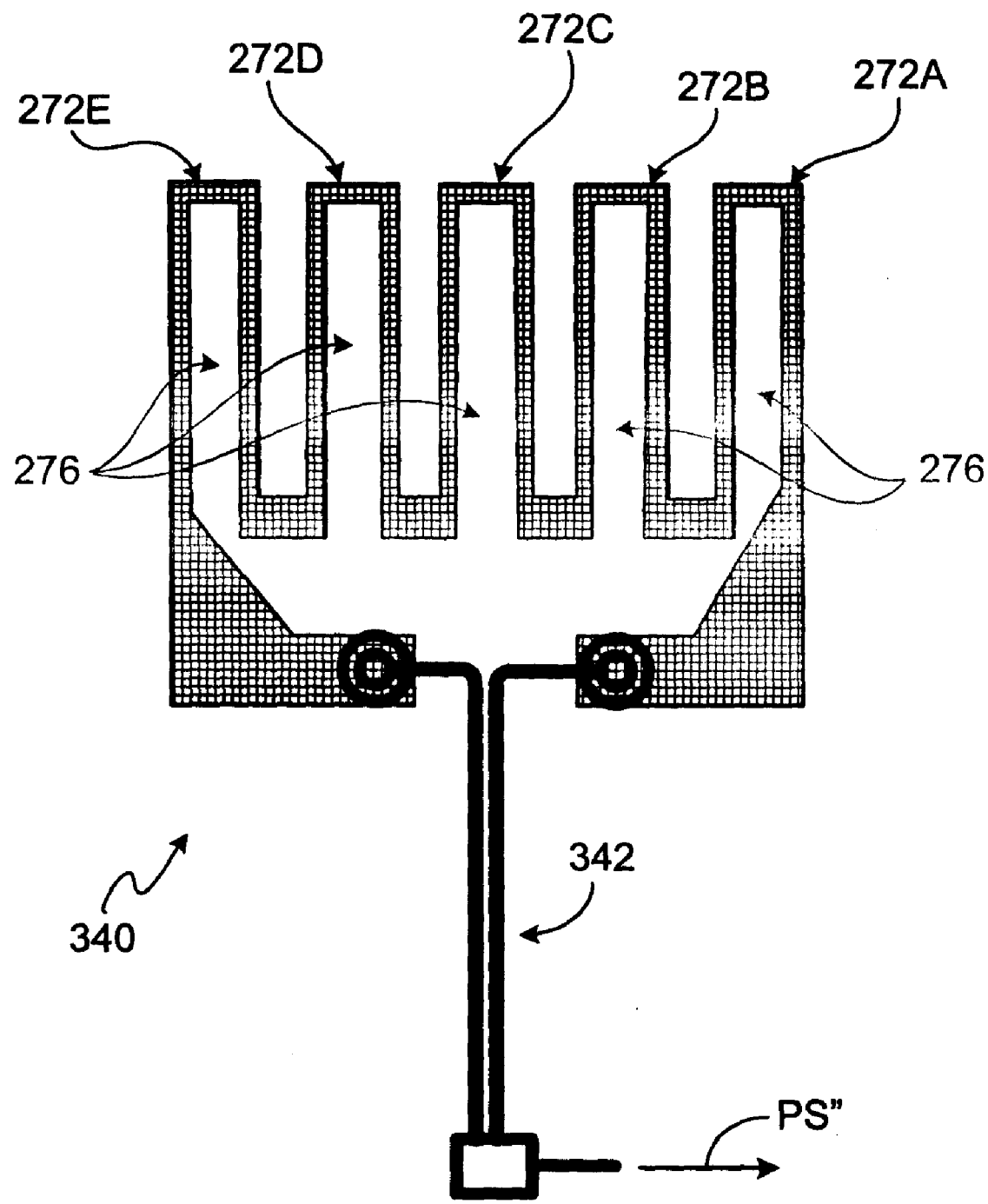
FIG. 26 is a somewhat diagrammatic front plan view of an article of footwear with another implementation of an electric heating/warming element of the disclosure.

Accordingly, other embodiments are within the scope of the invention. For example, although die cut materials are described other means can also be used to cut the conductive fabric. For example the fabric can also be laser cut or cut using ultra sound. Also, referring to FIG. 26, in an alternative implementation of the preferred heating element for use in footwear shown in FIG. 23, an electric heating/warming element 340 may be connected to a power source (arrow, PS") by a flat cable wire 342, e.g. in place of the bus sections 272 F, 272G shown in the implementation of FIG. 23.

What is claimed is:

1. A method of forming an electric heating/warming fabric article, the method comprising:

configuring a planar, sheet-form conductive layer element including a bus, formed of electrically conductive material selected from the group consisting of metallized textile, metallized plastic sheeting, and metal foil, into an electrically conductive circuit with shape corresponding to a selected surface region of a wearer's body and with one or more circuit regions of relatively higher resistivity among one or more circuit regions of relatively lower resistivity, the one or more circuit regions of relatively higher resistivity positioned for correlation with one or more selected heating regions of the wearer's body;

attaching said circuit to at least one of a first broad surface and a second broad surface of a fabric body in an arrangement corresponding to the selected surface region and in correlation with the one or more selected heating regions; and, upon application of electrical current to said circuit, producing localized heating in the one or more circuit regions of relatively higher resistivity of the circuit attached upon the fabric body for preferential heating of the one or more selected heating regions of the wearer's body.

2. The method of claim 1, further comprising configuring the planar, sheet-form conductive layer element including an integral bus.

3. The method of claim 2, further comprising impregnating the electrically conductive metallized textile with a suitable thermoplastic polymeric material to lock fibers of the electrically conductive metallized textile in a manner to resist local increase in resistivity due to physical stress from one or more of repeated crushing, bending and flexing.

4. The method of claim 3, further comprising applying the suitable thermoplastic polymeric material in fluid state and forming a fabric laminate incorporating the impregnated electrically conducting metallized textile.

5. The method of claim 4, further comprising forming a laminate of woven fabric.

6. The method of claim 5, further comprising forming a laminate of lightweight woven fabric stable in warp and fill directions.

7. The method of claim 3, further comprising at least partially impregnating the metallized textile application of predetermined conditions of heat, pressure and time to at least one layer of the suitable thermoplastic polymeric material in the form of a film disposed adjacent the metallized textile to be at least partially impregnated.

8. The method of claim 7, further comprising applying heat of about 350° F. at pressure of about 7 psi for about 50 seconds.

9. The method of claim 3, further comprising at least partially impregnating the metallized textile with a suitable thermoplastic polymeric barrier material having characteristics of being air-and-water-droplet resistant and being water vapor permeable.

10. The method of claim 9, further comprising at least partially impregnating the metallized textile with urethane.

11. The method of claim 1, wherein said configuring comprises die-cutting.

12. The method of claim 1, wherein said configuring comprises subjecting a sheet material to metal coating, plating or deposition.

13. The method of claim 1, wherein the attaching comprises joining the conductive layer and fabric body with adhesive.

14. The method of claim 1, further comprising forming an article of clothing including said fabric body.

15. The method of claim 14, wherein the forming comprises shaping the circuit to conform to the shape of the article of clothing.

16. The method of claim 14, wherein the forming comprises shaping the circuit to conform to the shape of the article of clothing comprising an article selected from the group consisting of gloves, socks, sweaters, jackets, shirts, pants, hats, footwear, ear muffs, neck warmers, medical braces, medical bands, knee pads, back pads, and joint pads.

17. The method of claim 14, wherein the forming comprises shaping the circuit to conform to the shape of a glove.

18. The method of claim 14, wherein the forming comprises shaping the circuit to conform to the shape of an article of footwear.

19. The method of claim 14, wherein the forming comprises shaping the circuit to conform to the shape of a garment such as a shirt or jacket.

20. The method of claim 1, further comprising providing circuit regions of relatively higher resistivity by reducing cross-sectional area of one or more selected regions of the circuit.

21. The method of claim 1, further comprising providing circuit regions of relatively higher resistivity by reducing conductivity of one or more selected regions of the circuit.

22. The method of claim 1, wherein the electric heating/warming article is incorporated into an article of clothing, and the method further comprises positioning the one or more circuit regions of relatively higher resistivity for correlation with one or more selected heating regions of the wearer's body adjacent the wearer's extremities when the article of clothing is worn.

23. The method of claim 1, wherein the method further comprises incorporating the electric heating/warming article into an article of clothing, and positioning the one or more circuit regions of relatively higher resistivity for correlation with one or more selected heating regions of the wearer's body adjacent regions of the wearer's body where blood flow is close to the skin surface when the article of clothing is worn.

24. The method of claim 1, wherein the attaching comprises attaching the circuit to at least one broad surface of a fabric body comprising a textile material selected from the group consisting of weft knitted materials, warp knitted materials, woven materials, and nonwoven materials.

25. The method of claim 1, wherein the method further comprises interposing an air-and-water-droplet resistant, water vapor permeable barrier layer between the fabric body and the sheet-form conductive layer.

26. The method of claim 25, further comprising attaching an outer surface of the air-and-water-droplet resistant, water vapor permeable barrier layer to the fabric layer, and attaching an inner surface of the barrier layer to the sheet-form conductive layer.

27. The method of claim 26, wherein the attaching comprises joining the layers with adhesive.

28. The method of claim 1, further comprising connecting the circuit to a power source, to generate heating/warming.

29. The method of claim 1, further comprising incorporating the electric heating/warming fabric article into a home furnishing textile article.

30. The method of claim 29, wherein the home textile article comprises a blanket, throw, sleeping bag or mattress cover.

31. The method of claim 1, wherein the configuring of the circuit comprises configuring the circuit as a series circuit.

32. The method of claim 1, wherein the configuring of the circuit comprises configuring the circuit as a parallel circuit.

33. The method of claim 1, further comprising providing at least one of the first broad surface and the second broad surface of the fabric body with a smooth surface.

34. The method of claim 1, further comprising providing at least one of the first broad surface and the second broad surface of the fabric body with a raised surface.

35. The method of claim 1, further comprising providing at least one of the first broad surface and the second broad surface of the fabric body with a brushed surface.

* * * * *

UNITED STATES PATENT AND TRADEMARK OFFICE
Certificate

Patent No. 7,777,156 B2                                                                  Patented: August 17, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Moshe Rock, Brookline, MA (US); Vincent Doyle, III, Pelham, NH (US); and Vikram Sharma, Stoneham, MA (US).

Signed and Sealed this Fifteenth of January 2013.

*HENRY YUEN*
*Supervisory Patent Examiner*
*Art Unit 3742*
*Technology Center 3700*